United States Patent
Klardie et al.

(10) Patent No.: US 7,204,692 B2
(45) Date of Patent: *Apr. 17, 2007

(54) IMPRESSION CAP

(75) Inventors: Michael R. Klardie, Bloomington, MN (US); Robert D. Carter, Apple Valley, MN (US); Peter B. Swenson, Eden Prairie, MN (US); Richard L. Tvedt, Savage, MN (US); John De Angelo, Hillsborough, NJ (US)

(73) Assignee: Lifecore Biomedical, Inc., Chaska, MN (US)

( * ) Notice: Subject to any disclaimer, the term of this patent is extended or adjusted under 35 U.S.C. 154(b) by 328 days.

This patent is subject to a terminal disclaimer.

(21) Appl. No.: 10/356,735

(22) Filed: Jan. 31, 2003

(65) Prior Publication Data

US 2003/0211445 A1 Nov. 13, 2003

Related U.S. Application Data

(63) Continuation-in-part of application No. 10/099,930, filed on Mar. 13, 2002.
(60) Provisional application No. 60/427,147, filed on Nov. 18, 2002.

(51) Int. Cl.
*A61C 8/00* (2006.01)
(52) U.S. Cl. .................................... 433/173
(58) Field of Classification Search ............... 433/173, 433/172, 175, 174, 221
See application file for complete search history.

(56) References Cited

U.S. PATENT DOCUMENTS

| | | | | |
|---|---|---|---|---|
| 5,458,488 A | * | 10/1995 | Chalifoux | .................. 433/173 |
| 5,681,167 A | | 10/1997 | Lazarof | |
| 5,762,500 A | | 6/1998 | Lazarof | |
| 6,068,478 A | * | 5/2000 | Grande et al. | .............. 433/172 |
| 6,142,782 A | | 11/2000 | Lazarof | |
| 2001/0034008 A1 | | 10/2001 | Porter et al. | |
| 2002/0004189 A1 | | 1/2002 | Hurson | |
| 2002/0106610 A1 | | 8/2002 | Hurson | |
| 2003/0082499 A1 | * | 5/2003 | Halldin et al. | .............. 433/173 |

FOREIGN PATENT DOCUMENTS

WO    WO 02/17814 A1    3/2002

* cited by examiner

*Primary Examiner*—Melba Bumgarner
(74) *Attorney, Agent, or Firm*—Dorsey & Whitney LLP

(57) ABSTRACT

The present invention is an impression cap for use with an implant/abutment impressioning system for taking impressions of cement-on-crown abutments to mirror the contour of the soft tissue and bone in a patient's mouth. The impression cap is configured to uniquely fit over one of an abutment and a dental implant via a novel flange. The flange is located at the bottom of the impression cap forming a bottom rim and is constructed to grasp the collar of an implant in a press, friction fit manner. The flange of the impression cap automatically captures the implant margin by pushing gingival tissue away when the component is seated.

16 Claims, 26 Drawing Sheets

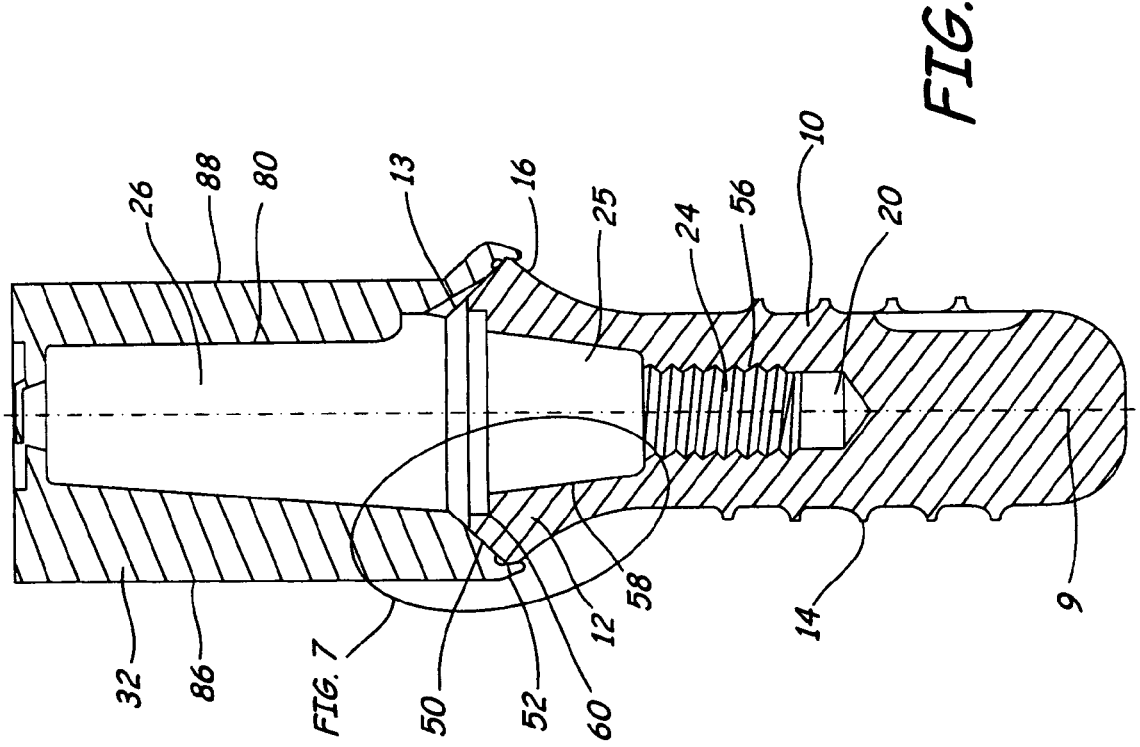

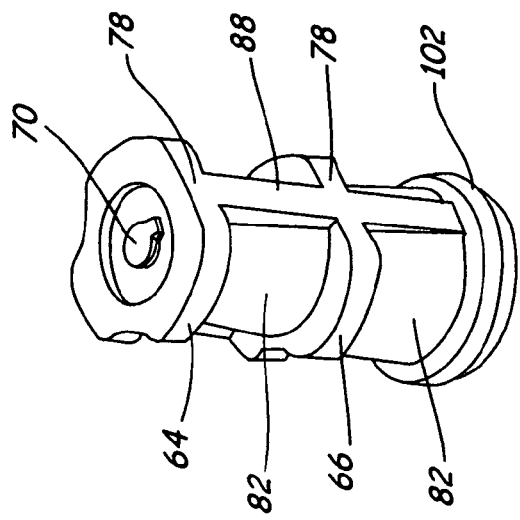
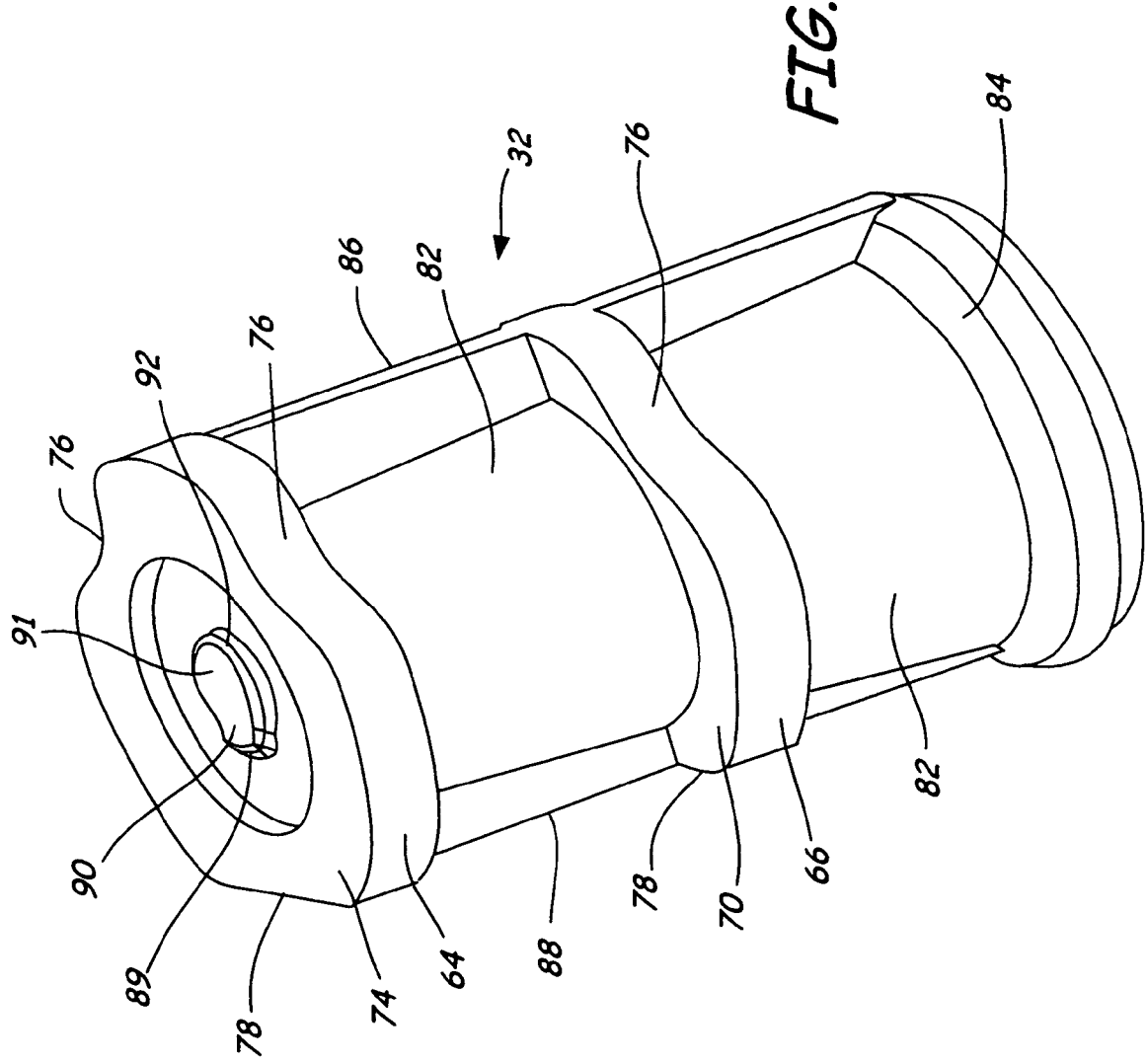

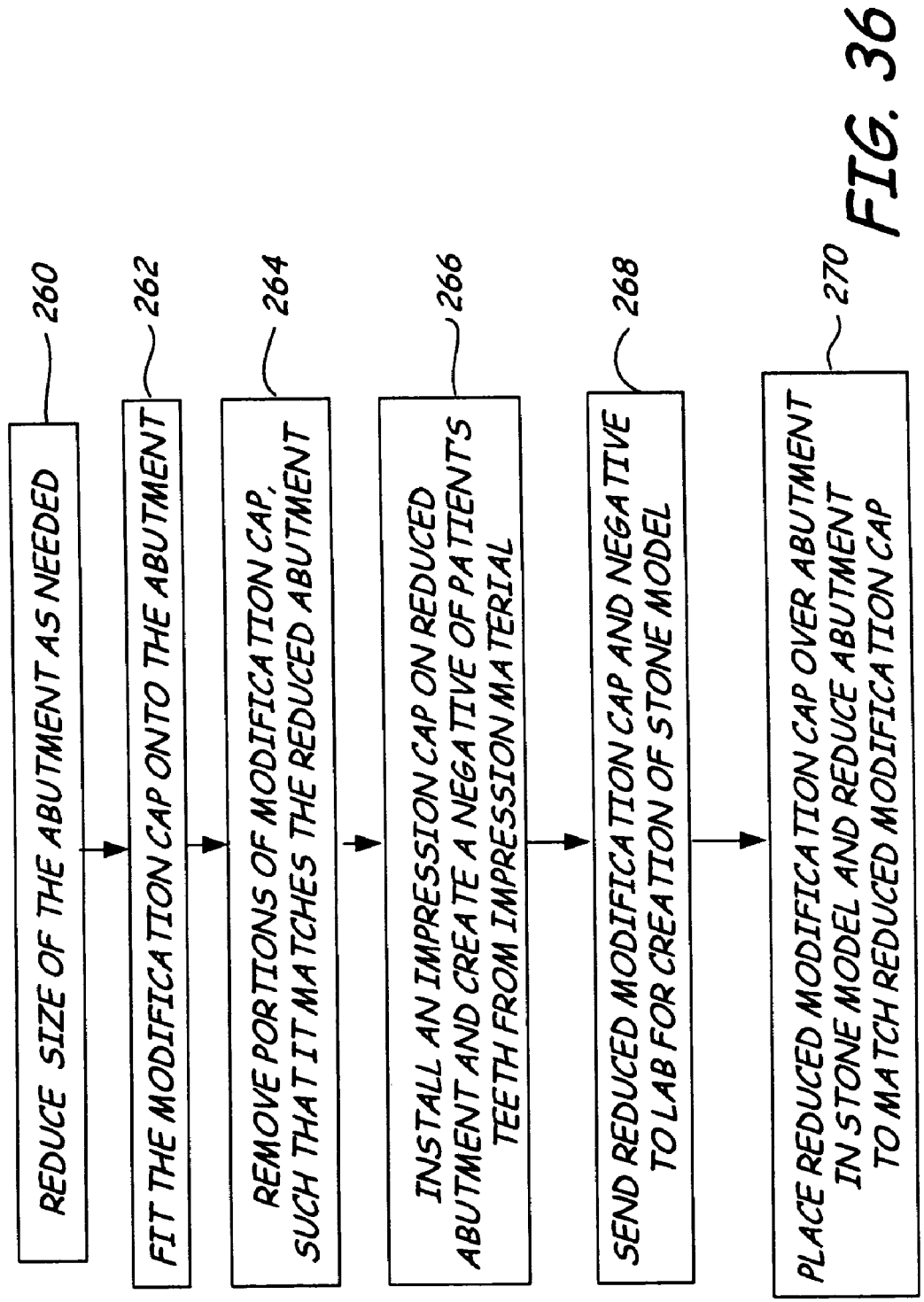

IMPRESSION CAP

CROSS-REFERENCE TO RELATED APPLICATION(S)

This application is a continuation-in-part of U.S. patent application Ser. No. 10/099,930, filed Mar. 13, 2002, which is hereby incorporated by reference, and claims priority to U.S. provisional patent application No. 60/427,147, filed Nov. 18, 2002.

FIELD OF THE INVENTION

The present invention relates to an Implant/Abutment Impressioning System with a novel impression cap for an implant fitted in the human body in order to transfer the implant end protruding from the tissue structure to a master cast.

BACKGROUND

The following discussion refers in the first instance to the example of dental implants. For taking an impression of the situation in the patient's mouth and for transferring the impression obtained to a master cast, on which the tooth replacement is then modeled, a number of elements have hitherto been used. The work steps that have had to be performed, and the elements used in these work steps, are dealt with in detail by SCHROEDER, A.; SUTTER, F.; BUSER, D.; KREKELER, G.: Orale Implamologie [Oral implantology], Georg Thieme Verlag Stuttgart, 2nd edition, 1994, page 202 et seq. On the one hand, the assembling of the elements in the patient's mouth, particularly in the area of the molars, is problematic because of the resulting overall height of the elements, especially if a screwing instrument has to be used as well. Moreover, the work procedures are demanding for the patient, and they are time-consuming as regards impression-taking and production of the master cast. In addition to this, inaccuracies occur. The difficulties result primarily from the fact that the impression cap does not hold itself on the implant fitted in the mouth or on the manipulation implant to be used subsequently in the production of the master cast. DE 44 15 670 A1 discloses an impression cap which, at the open end facing the implant, has resilient flaps which, when applied, engage over the shoulder of the conical superstructure, the latter being fitted into the implant. The impression cap described there cannot therefore be used for taking an impression of the implant end protruding from the gingiva and projecting into the mouth, but instead only for taking an impression of the outer contour of the superstructure while the implant is positioned below the gingiva.

U.S. Pat. No. 6,068,478 discloses alternatives to the prior impression/implant systems. U.S. Pat. No. 6,068,478 describes an impression system which comprises as its principal component an impression cap for transferring an end, protruding from a human tissue structure, of an implant which is fitted in the human body, including possible superstructures, to a master cast. The outwardly directed implant end has an undercut contour on its outside, and the impression cap has a geometry which complements the undercut contour and engages therein. The undercut contour is formed either by an implant geometry tapering in a trumpet shape towards the implant bed, or by a recess near the implant end. After the impression cap is secured to the implant, it is encased in impression material. The impression cap embedded in the impression compound present in the impression tray is removed from the fitted implant and receives a manipulation implant to make a master cast.

Two main types of surgical procedures are used in the field to accomplish placement of dental implants in a patient's mouth. In the first procedure, known as single-stage implantation, the dental implant has a threaded portion and a head. A hole is drilled into the underlying bone structure (i.e., the maxilla or the mandible), and the threaded portion is threaded into the hole. The head portion of the implant extends through the gingiva such that the top surface of the head protrudes slightly. The gingiva is then sutured around the head of the implant. After a sufficient length of time for healing, the patient then returns for creation of a master cast.

In the second procedure, known as a two-stage implantation, the dental implant again has a threaded portion and a head. In the two-stage procedure, however, the head of the implant extends slightly above the underlying bone structure and under the surface of the gingiva. After placement of the implant and suturing of the gingiva, the patient is given time for healing. The patient then returns and the gingiva is opened above the implant to allow for placement of an abutment. The abutment employed in the two-stage process has a cuff or base and an abutment post protruding upwardly from the cuff. The cuff is sized such that it ends at a level slightly above the gingiva. Typically, the abutment used in the two-stage process is attached to the implant by threading a screw through a longitudinal bore of the abutment and into the implant. After a further time period for healing, the patient returns for creation of a master cast.

The present invention addresses further constructive alternatives to the prior impression/implant systems. All U.S. patents, patent applications, and other published documents, mentioned anywhere in this application, are incorporated herein by reference in their entirety.

BRIEF SUMMARY OF THE INVENTION

The present invention, in one embodiment, relates to an impression cap for use with an implant/abutment impressioning system for taking impressions of cement-on-crown abutments to mirror the contour of the soft tissue and bone, in a patient's mouth, as accurately as possible. More particularly, the invention discloses a novel impression cap including a novel retention system for retaining the impression cap to the implant or abutment during the taking of impressions and to the analog during the formation of a stone model. The impression cap is configured to uniquely fit over an implant (in a single-stage implantation) or over an abutment in an abutment/implant assembly (in a two-stage implantation) and grasp the implant or the abutment via a novel flange and internal geometrical design. The flange is located at the bottom of the impression cap forming a bottom rim and is constructed to grasp the collar of an implant or an abutment in a press/friction fit manner. The internal geometry of the impression cap forms surfaces which substantially mirror portions of corresponding external surfaces of the abutment or the abutment/implant assembly. The flange of the impression cap automatically captures the implant or abutment margin by pushing gingival tissue away when the component is seated. This eliminates the need to pack cord, a common but tedious dental procedure.

The retention system of the present invention is applicable both to a closed impression cap having a substantially closed interior configuration or to an open impression cap in which the cap includes a basket or open structure allowing impression material to form around the implant or the abutment.

The preferred embodiment, however, will be described with respect to a closed impression cap.

According to one embodiment, the present invention is an impression cap for coupling to one of a dental abutment or dental implant in which the abutment or the implant includes a collar with a peripheral retention edge having an outer diameter. The impression cap includes a body having a first end for coupling to the abutment or implant. The body further includes a retention flange at said first end, with the flange having an inner surface engageable with the retention edge of the abutment or implant. To accomplish this retaining engagement, such inner surface has an inside diameter equal to or slightly less than the outer diameter of the retention edge, such that the flange forms a friction fit with the retention edge.

Another embodiment of the present invention is a reduction-coping method for communicating certain modifications to the size or shape of a dental abutment. The method comprises modifying the abutment or abutment post as desired to create a modified abutment and forming a modified impression cap to match the modified abutment. To form the modified impression cap, a modification cap, in the form of an unmodified impression cap or other structure, is positioned over the modified abutment and reduced to correspond to the modified abutment or the modification cap is positioned over an unmodified abutment and the two are reduced together. The reduced modification cap is then used as a pattern to create a duplicate of the modified abutment, with the duplicate having an external geometry having a size and shape substantially matching that of the modified abutment.

The present invention, according to another embodiment, is a method of creating a temporary crown to cover an abutment attached to a dental implant in a patient's mouth. The method comprises providing an impression cap having a first end connectable to one of the dental implant or the abutment and having an internal opening forming an interval cavity sized to receive the abutment. A temporary crown is formed on the impression cap. The impression cap, with formed crown, is then attached to the dental implant or the abutment.

BRIEF DESCRIPTION OF THE DRAWINGS

FIG. 6 is a cut-away view showing a partial cross-section of an implant/abutment assembly and an impression cap mounted thereon;

FIG. 8 is a view of an impression cap;

FIG. 8A is a view of an impression cap;

FIG. 36 is a flowchart showing a process for performing reduction coping on an abutment, according to one embodiment of the present invention.

DETAILED DESCRIPTION

Figure 1:
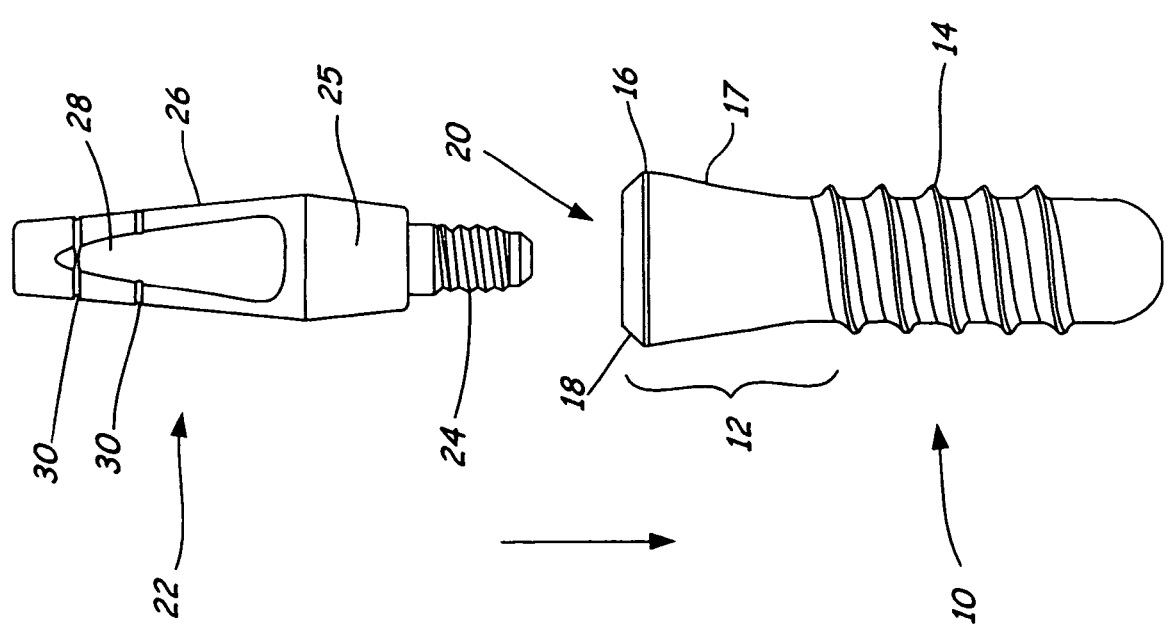
FIG. 1 is an implant and an abutment in an exploded view.

The present invention relates to the taking of an impression of an implant 10 fitted in the mouth of a patient, here a dental implant as a full screw. As shown in FIG. 1, the implant 10 has an implant head 12 which includes an outer surface 17 that widens conically upwardly and a plurality of threads 14 for insertion into the patient. The implant head 12, which will be shown in detail in later figures, includes an implant collar 16 having a retention edge and an angled implant surface or shoulder 18. An internal threaded bore 20 is also formed in the implant 10.

An abutment 22 is screwed into the implant 10 via its threaded part 24 into the internal threaded bore 20 of the implant 10, as further shown in FIG. 1. The abutment 22 has a base 25 and an abutment post or portion 26, which is generally conical and has a female abutment flat 28. The abutment post 26 may have one or more abutment flats 28. An abutment flat 28 is a flat surface formed by a generally vertically extending recess or groove used to prevent rotation when further pieces are placed over the abutment post 26.

The abutment post 26 also has one or more circumferential grooves 30. The grooves provide additional retention of the crown after cementing. They also may be used to indicate the height of the abutment so that the user may determine the appropriate cap. Typical heights include 4.0 mm and 5.5 mm. The height of the abutment post 26 is such that it extends upwardly to a point generally located between about one half and the full height of the surrounding teeth. Such a height will provide adequate structure to which a crown can be mounted securely and not extend above the surrounding teeth.

Figure 2:
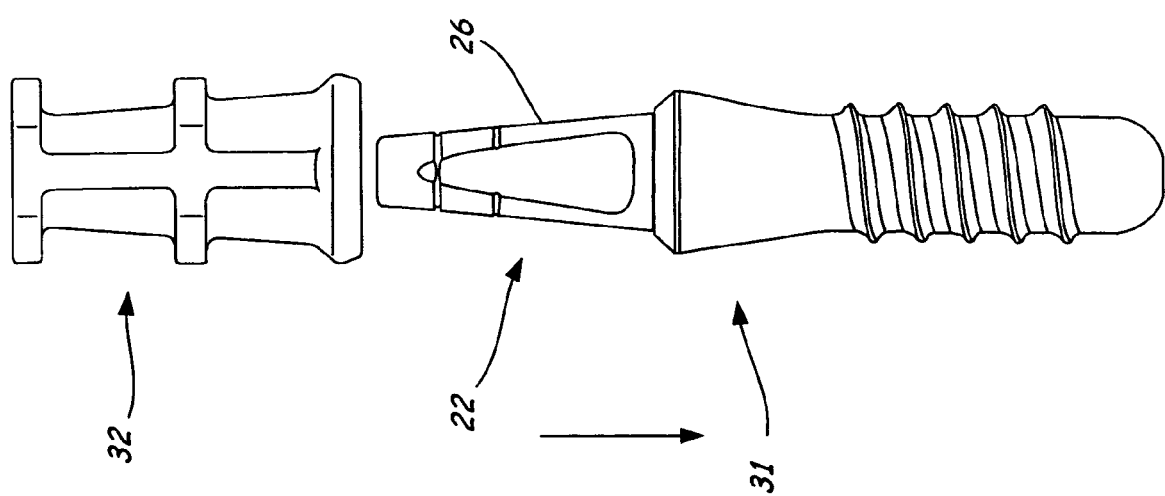
FIG. 2 is an implant/abutment assembly and an impression cap in an exploded view.
Figure 3:
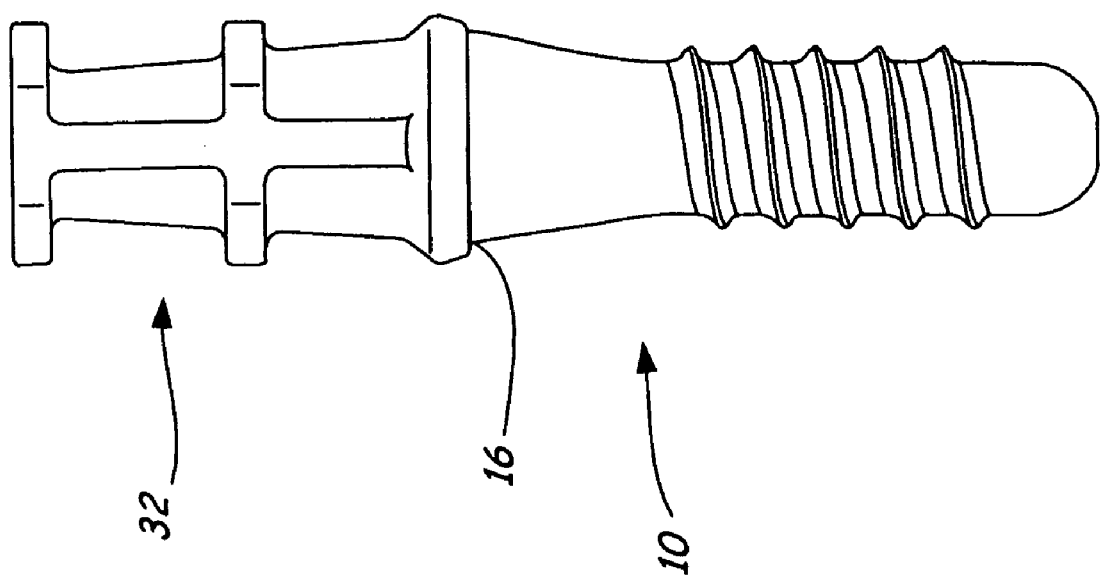
FIG. 3 is an implant/abutment assembly and an impression cap mounted thereon.

FIG. 2 shows the abutment 22 screwed into the implant 10 to form an abutment/implant assembly 31. An impression cap 32 is then lowered over the abutment post 26. As will be shown below, the internal geometry of the impression cap 32 is configured to uniformly fit over the post 26. FIG. 3 illustrates the impression cap 32 lowered onto the abutment 22.

In FIG. 3, the impression cap 32 press fits down over the collar 16 of the implant 10 to capture the implant margin and position. Impression material is then placed over and around the installed impression cap 32 to take an impression of the gum around the abutment/implant assembly. The impression material, with the impression cap embedded therein, is then removed from the abutment/implant assembly and the patient. Thus, the impression cap 32 remains is the impression material when it is removed.

Figure 4:
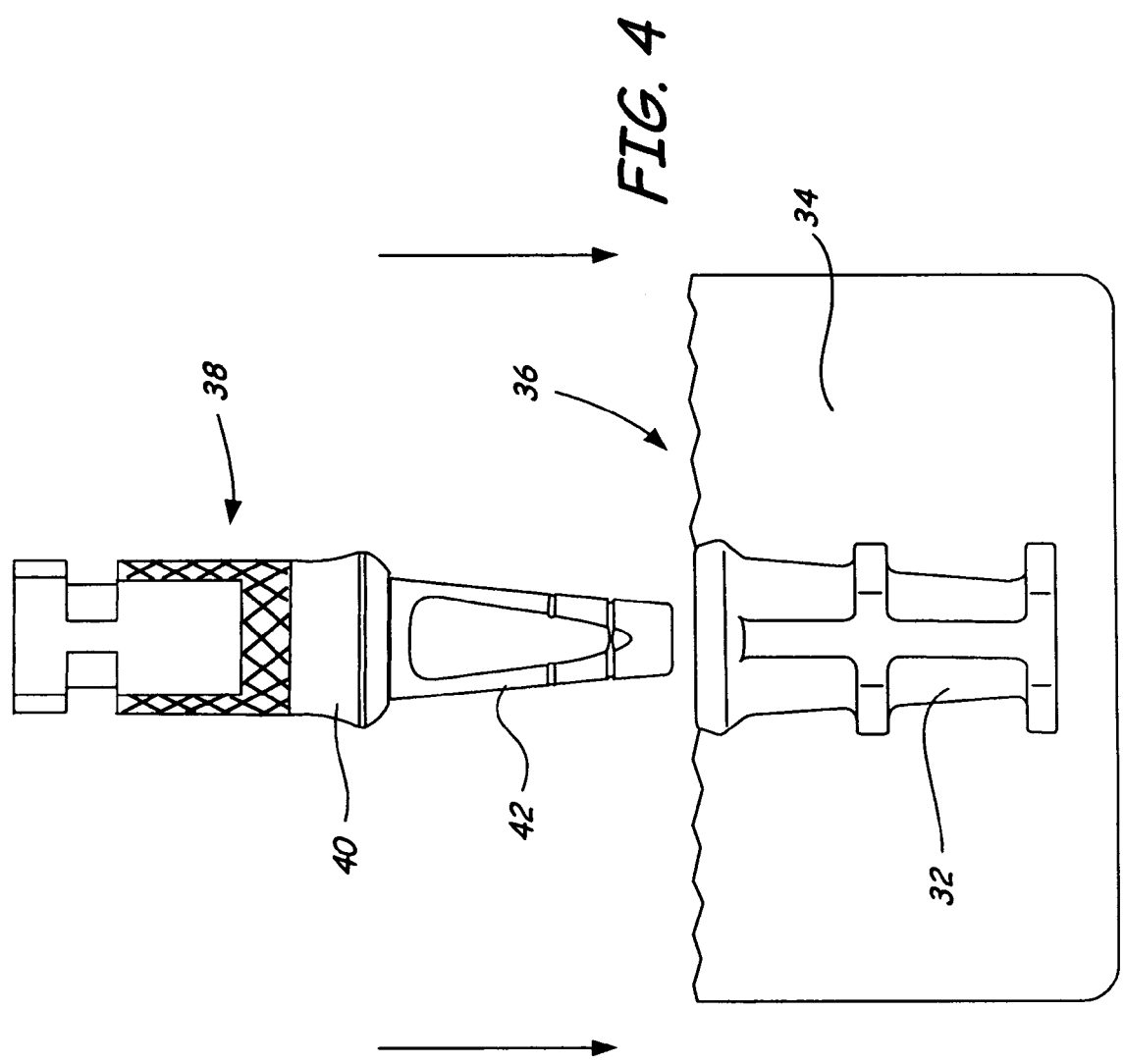
FIG. 4 is an abutment in an impression material tray and an analog in an exploded view.

FIG. 4 shows the removed impression cap 32 in the impression material 34. A negative 36 of the gum surface is formed in the impression material 34. An analog 38 is then inserted into the impression cap 32. The analog 38 has a handle 39, a head 40 and an abutment post 42. The head 40 and the abutment post 42 mimic the shape of the head 12 and the abutment post 26 of the implant 10. This provides a fit which replicates the fit between the impression cap 32 and the abutment/implant assembly 31.

Figure 5:
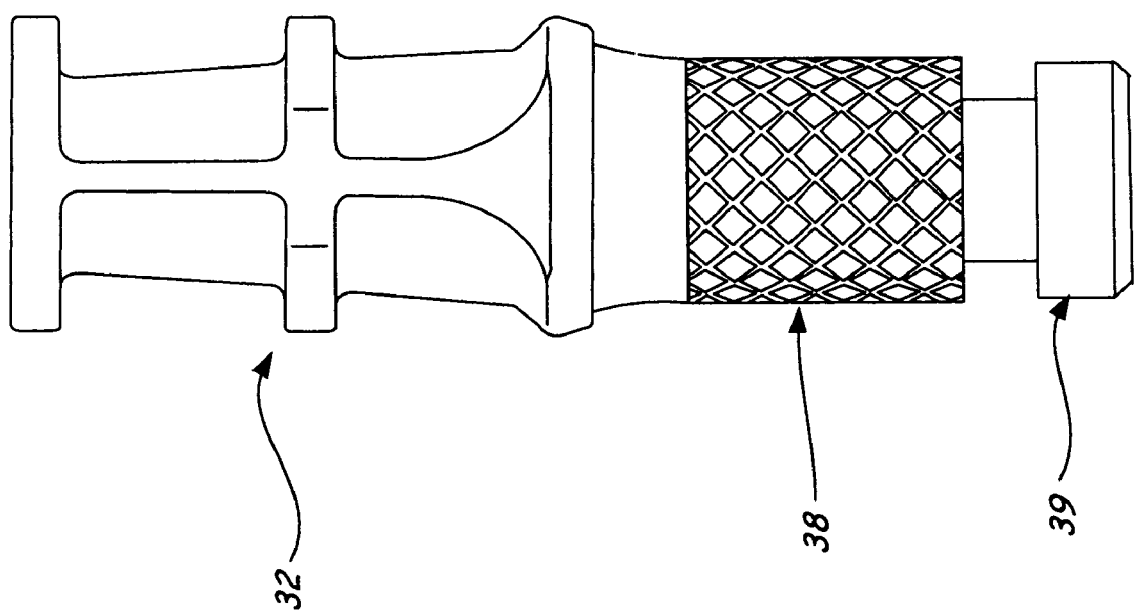
FIG. 5 is an abutment in an impression material tray and an analog in an assembled view.

FIG. 5 shows the engagement between the impression cap 32 within the impression material (not shown) and the analog 38. Stone model material is then poured over and around the analog 38 and onto the surface of the impression material 36. This material is then allowed to harden to create a stone model. After the material sufficiently hardens, the impression cap 32 and the impression material 36 are removed, leaving the analog 38 and the newly formed stone model. The stone model has an outer surface which mimics the surface of the gum line around the inserted abutment/implant assembly 31. The analog 38 remains fixed in the stone model and together they replicate the position of the Cement-on-Crown Abutment that is in the patient's mouth. This apparatus may be used for future construction of dental implants which will fit uniformly in the patient's mouth.

Further discussion will address particular components of the Implant/Abutment Impressioning System.

Figure 7A:
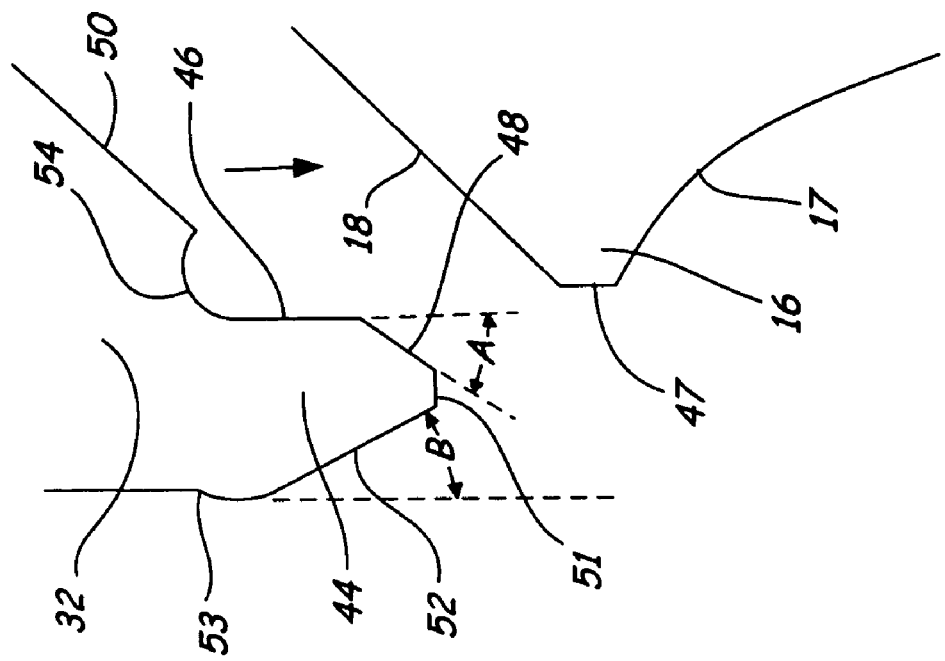
FIG. 7A is an enlarged view, partially in section, showing the retaining engagement between the impression cap and an implant.
Figure 7:
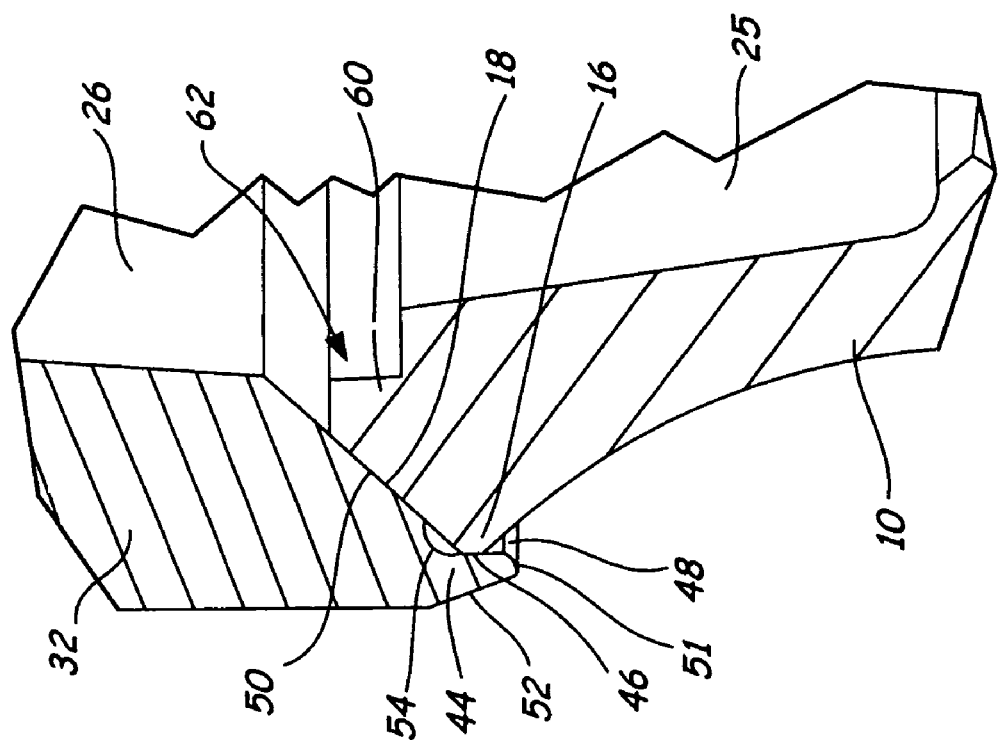
FIG. 7 is a detailed cut-away view showing a partial cross-section of a portion of FIG. 6, as indicated.

FIG. 6 illustrates a cross-sectional view of FIG. 3. The device is positioned to view the abutment flat 28 from the side. In this figure, the abutment 22 is screwed into the implant 10 and the impression cap 32 is positioned on the abutment post 26. FIGS. 6, 7, and 7A illustrate the fit between the impression cap 32 and the abutment/implant assembly 31, as well as the fit between the abutment 22 and the implant 10.

FIGS. 7 and 7A are enlarged views of a portion of FIG. 6. Except for a secondary vent 13, which will be discussed below, FIG. 7 illustrates the engagement between the press fit or friction fit mechanism of the impression cap 32 and the implant 10, while FIG. 7A represents the same view, but with the implant and abutment in position prior to engagement. This engagement occurs primarily between the peripheral portions of the implant collar 16 and the engagement end or press fit mechanism of the impression cap 32. The press fit or friction fit mechanism of the impression cap provides an inwardly directed radial force against the periphery of the collar 16.

As shown in FIGS. 7 and 7A, at the engagement end, the press fit mechanism of the impression cap 32 has a circumferential flange 44 to guide the engagement end of the impression cap 32 over the implant collar. The flange 44 has a press or squeeze surface 46 which engages the outer periphery of the collar 16. Preferably, the surface 46 is cylindrical with its side walls substantially parallel to the axis 9 of the implant 10. In this preferred structure, the surface 46 preferably has a length dimension, and more particularly a cylindrical length dimension, measured in a direction parallel to the implant axis, of about 0.010 inches to about 0.035 inches and more preferably about 0.020 inches to about 0.025 inches.

In the preferred embodiment, the outer periphery of the collar 16 includes an outer peripheral retention edge 47. The edge 47 defines the maximum diameter of implant collar 16. Preferably, the edge 47 has an outer cylindrical surface portion with a length dimension measured parallel to the implant axis of about 0.004 inches to about 0.010 inches, and no less than about 0.003 inches. The above length dimension of the edge is preferably shorter than the corresponding length dimension of the surface 46. The connection between the flange 44 and the collar 16 is a pressure frictional fit, wherein the flange 44 squeezes or exerts a force against the outer surface or retention edge 47 of the collar 16. Although as described above, the retention edge 47 which contacts the flange 44 may be flat and of cylindrical configuration to provide a greater contact surface, the edge 47 may also terminate at a point or be provided with other cross-section configurations, if desired.

Although the surface 46 is preferably cylindrical as described above, the surface 46 may also slope inwardly, or have a portion that slopes inwardly as it extends downwardly. In such an embodiment, the surface 46 would still include at least a portion, and preferably a generally cylindrical portion, which engages only the retention edge 47. In this embodiment, no portion of the surface 46 would engage any portion of the sloping outer surface 17 of the head 12.

The flange 44 further includes a lead in taper in the form of a tapered surface 48 to guide the flange 44 over the collar 16 so that the surface 46 engages the edge 47. During assembly of the impression cap 32 onto the implant 10, the tapered surface 48 contacts the outer surface or edge 47 of the implant collar 16 first. This initial contact helps expand the flange 44 of the impression cap 32 so that the press surface 46 can press fit (or friction fit) against the maximum diameter (the retention edge 47) of the implant collar 16. The lead in tapered surface 48 can be a chamfer, radius, or the like. In one embodiment, this tapered surface 48 tapers downwardly and outwardly from the edge 47 at an angle "A" of about 30 degrees to about 60 degrees and terminates at the lowermost end 51 of the flange 44 and the impression cap. In another embodiment, the angle "A," formed by the tapered surface 48 is from about 40 degrees to about 50 degrees.

The impression cap 32 also comprises an angled surface 50 which engages and thus provides a reference stop with the angled shoulder 18 of the implant 10. This surface 50 to surface 18 contact provides a consistently accurate means of determining that the impression cap 32 is fully seated on the implant/abutment assembly 31. When the angled surface 50 contacts the implant shoulder surface 18, it produces a tactile feel, which indicates to the user that the impression cap 32 is fully seated. When the impression cap 32 and implant 10 are fully seated, the angled surfaces (50 & 18), provide stability by aligning and self-centering the impression cap 32 on the implant 10.

The flange 44 further includes an exterior angled surface 52 formed near its lower end. This surface 52 extends from the lowermost end 51 upwardly and outwardly where it is joined with the outer surface of the impression cap at the upper end of the flange 44. In one embodiment, the angle "B" which the surface 52 forms with the implant axis is about 15 degrees to about 30 degrees. In another embodiment, the angle "B," formed by the surface 52 is from about 20 degrees to about 25 degrees. During installation of the impression cap, the surface 52 pushes or retracts the gingival tissue away from the implant table. This allows the impression cap 32 to automatically capture the implant margin, or collar 16. This also eliminates the need to pack cord, a common but tedious dental procedure.

Because the impression cap is retained relative to the implant head and more specifically relative to the retention edge 47 via a press or friction fit, the retaining force between these two elements will be directly proportional to the amount of surface contact between the surface 46 and the edge 47 and the amount of force exerted by the flange 44 radially inwardly against the edge 47. The amount of force exerted by the flange 44 will in turn be dictated by the extent of interference or dimensional difference between the outer diameter of the edge 47 and the inner diameter of the surface 46. The amount of this radially inwardly directed force for a given dimensional interference, will also be dictated in part by the flexibility and thus the geometry of the flange 44.

In general, the retaining force between the impression cap and the implant for an installed impression cap should preferably be sufficient to retain the cap on the implant, and to prevent its inadvertent displacement or removal, during the application of the impression molding material and creation of the impression mold as described in greater detail below. To achieve this retaining force, the inner diametrical dimension of the surface 46 should preferably be about 0.004 inches to about 0.008 inches less than the outer diametrical dimension of the edge 47, which is equivalent to an interference dimension of about 0.002 inches to about 0.004 inches. More preferably, this interference dimension should be about 0.0025 inches to about 0.0035 inches. Also, when the impression cap is installed on the implant as shown in FIG. 7, the point at which the edge 47 engages the surface 46 should be below the upper end of the surface 46 and below the point 53 (FIG. 7A) at which the tapered surface 52 joins with the outer surface of the impression cap 32. Also, in one embodiment, the thickness dimension of the flange 44 measured in a generally radial direction at the midpoint of the surface 46 ranges from about 0.01 inches to about 0.02 inches. In another embodiment, the thickness dimension of the flange 44 measured in a generally radial direction at the midpoint of the surface 46 ranges from about 0.011 inches to about 0.016 inches. It has been found that the geometry of the flange 44 relative to the implant structure and with the above preferred dimensions and angles creates an acceptable retaining force.

The engagement end of the impression cap 32 also forms a curved relief 54 between the angled surface 50 and the surface 46 of the flange 44. Because the diametrical dimension of the surface 46 is slightly less than that of the edge 47 as discussed above, installation of the impression cap causes the surface 46 to be forced outwardly relative to the surface 50, thereby creating a stress at the juncture of such surfaces. This relief 54 removes such stresses formed between the press surface 46 and the angled or stop surface 50. The curved relief 54 also removes any stress risers that may occur within the material during installation of the impression cap as the lead in taper 48 moves over the implant collar.

FIGS. 6 and 7 further shows the fit between the abutment 22 and the implant 10. The implant 10 has a bored hole 20, which is partially threaded 56, partially conical 58 and partially stepped 60. These portions are mirrored by portions 24, 25 and 62 of the abutment 22 for a secure fit. The specific mirroring configurations are not critical as long as there is a snug fit between the implant 10 and the abutment 22.

FIG. 8 is a view of the outside of the impression cap 32. The outside of the impression cap 32 has contoured retention geometry (CRG). This CRG provides tension and compression resistance when the cap 32 is encased in impression material. The CRG comprises circumferential retention ribs 64 & 66 located at the top 64 and midway down 66 the exterior of the impression cap 32. Surfaces 68, 70, 72, & 74 (68 and 72 shown in FIG. 9) provide further tension and compression resistance when the cap 32 is encased in impression material.

The retention geometry also comprises one or more concave surfaces 76 to provide anti-rotation while encased within the impression material. The embodiment shown in FIG. 8 illustrates the concave surfaces 76 as being formed in the circumferential retention ribs 64, 66.

Anti-rotation is further provided by one or more flat surfaces 78, which are formed in retention ribs 64 and 66. Flat surfaces 78 within the retention geometry are aligned with internal flat 80 (shown in FIG. 9). This allows the flat surfaces 78 to be an indicator of the internal flat's 80 location. The flat surfaces can better be seen in FIG. 8a.

Generally, the impression cap 32 has a tapered body 82. The tapered body 82 allows surface area 72 on the upper retention rib 64 to be greater than the surface area 70 on the lower retention rib 66. It also allows the surface area 70 on the top of retention rib 66 to be greater than the surface area 68 on the bottom of retention rib 66. The increased surface area on the retention ribs 64, 66 allows for increased retention of impression cap 32 while encased within the impression material.

The tapered body 82 allows an increased amount of impression material to reside between the upper and lower retention ribs 64, 66 and between the lower retention rib 66 and angled surface 84. The increased impression material allows for increased retention of the impression cap 32 while encased within the impression material.

The impression cap 32 further comprises two vertical ribs 86, 88. Suitably these vertical ribs are located 180 degrees apart, relative to a center line through the cap 32 from the top to bottom. Vertical ribs 86 and 88 aid in strengthening the impression cap structure so that the impression cap 32 is not deformed from the compressive force imparted on it during seating of the impression cap 32 on the abutment/implant 31.

Vertical ribs 86, 88 also provide resistance to rotational movement of the impression cap 32 while encased within the impression material. In this embodiment, the vertical rib 86 has a greater horizontal depth than vertical rib 88 due to the presence of the flat surfaces 78. Both ribs 86, 88, have increasing horizontal depth from bottom to top for structural stability and for greater contact with the impression material. Vertical rib 88 extends downward from the center of the flat surface 78 and perpendicular to internal flat 80. This allows the vertical rib 88 to be an indicator of the internal flat's 80 location.

The impression cap 32 further comprises a one way vent 90 having a gap 92 for release of air during assembly. During the impressioning process when the impression material covers the cap, the impression material pushes against the vent 90 and seals gap 92. The seal does not allow impression material to enter the internal cavity 94 and no longer allows air to release.

Figure 9:
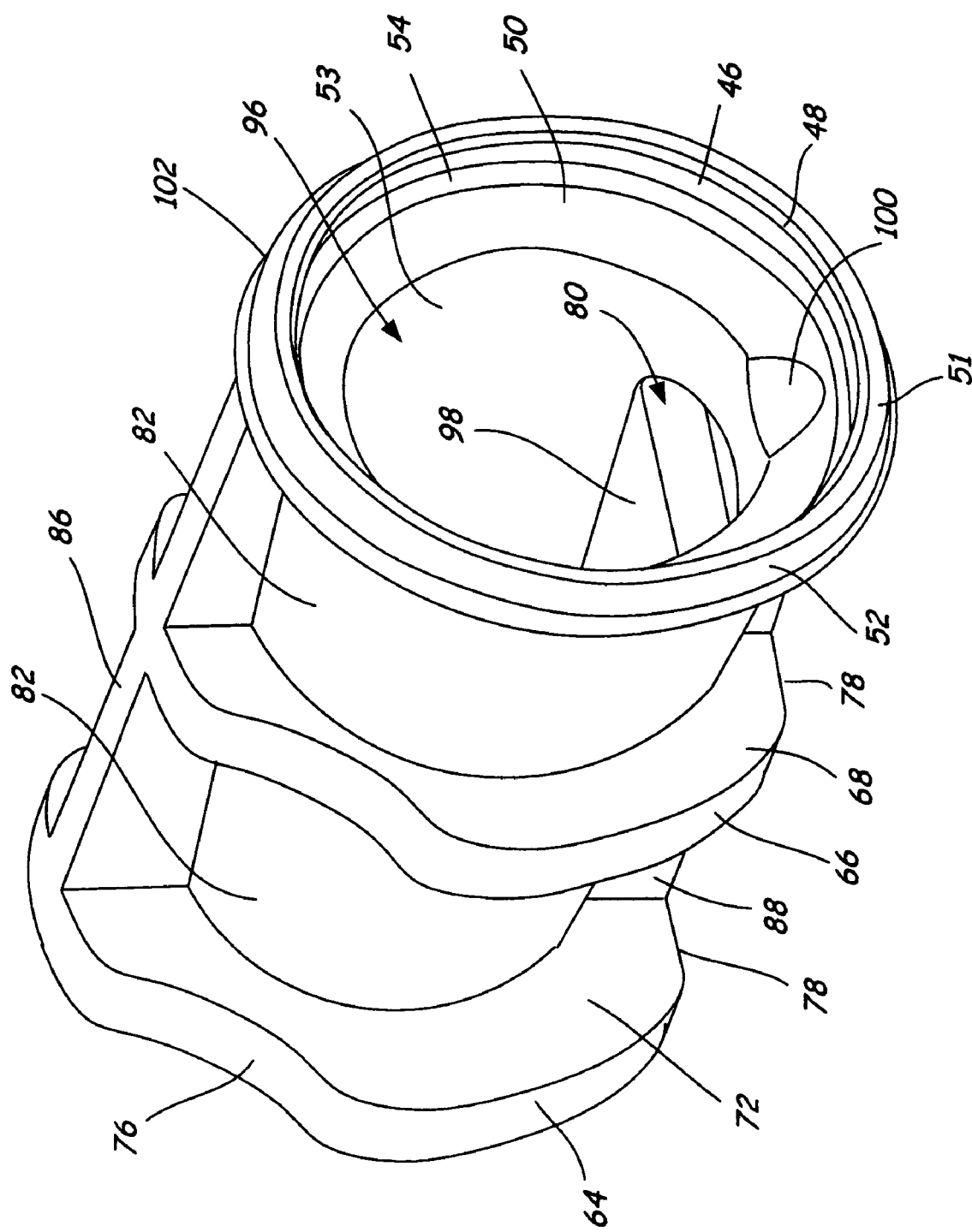
FIG. 9 is a view of an impression cap.

FIG. 9 illustrates a view of the impression cap 32 from a further angle showing a portion of the internal geometry of the inner cavity 96. The internal geometry of the impression cap 32 matches the geometry of the abutment/implant connection 31. Internal or abutment flat 80, which has an inner surface 98, interrupts the inner surface 53 of the cap. The abutment flat 80 provides anti-rotation and rotational stability.

The impression cap 32 further comprises a channel 100 which forms the secondary vent 13 when the cap 32 is coupled with the abutment/implant assembly 31. While assembling the impression cap 32 to the abutment/implant 31, air compresses within the internal cavity 96 of the impression cap. The compressed air pushes against the impression cap 32 and causes the impression cap 32 to lift off the abutment/implant 31. Air pressure relief (release) is beneficial to alleviating the internal air pressure.

The secondary vent 13 is a relief passage from the internal cavity 96 to the outside. The secondary vent 13 is a relief passage in the reference stop surface 50. This allows the majority of the trapped air to escape during assembly of the impression cap 32 to the abutment/implant configuration 31.

Although only one channel 100 is shown, it should be understood that the invention contemplates a plurality of channels arranged around the angled surface 50. For example, an embodiment may have a channel 100 as shown in FIG. 9 and a second channel situated 180 degrees around the angled surface and aligned with rib 86.

FIG. 9 also illustrates the bottom rim 102 showing the surfaces which form the flange 44 of the cap 32. The curved relief 54 follows the angle surface 50 from the inside of the cap 32 toward the outside. The pressing surface is shown at 46, followed by the lead in taper 48. Angled surface 52 represents the outer part of the flange 44. The flange 44 may have an extra surface 51 between angled surface 52 and surface 48 to provide a blunt end to the flange 44. Surface 51 may be substantially perpendicular to pressing surface 46 or rounded.

Figure 10:
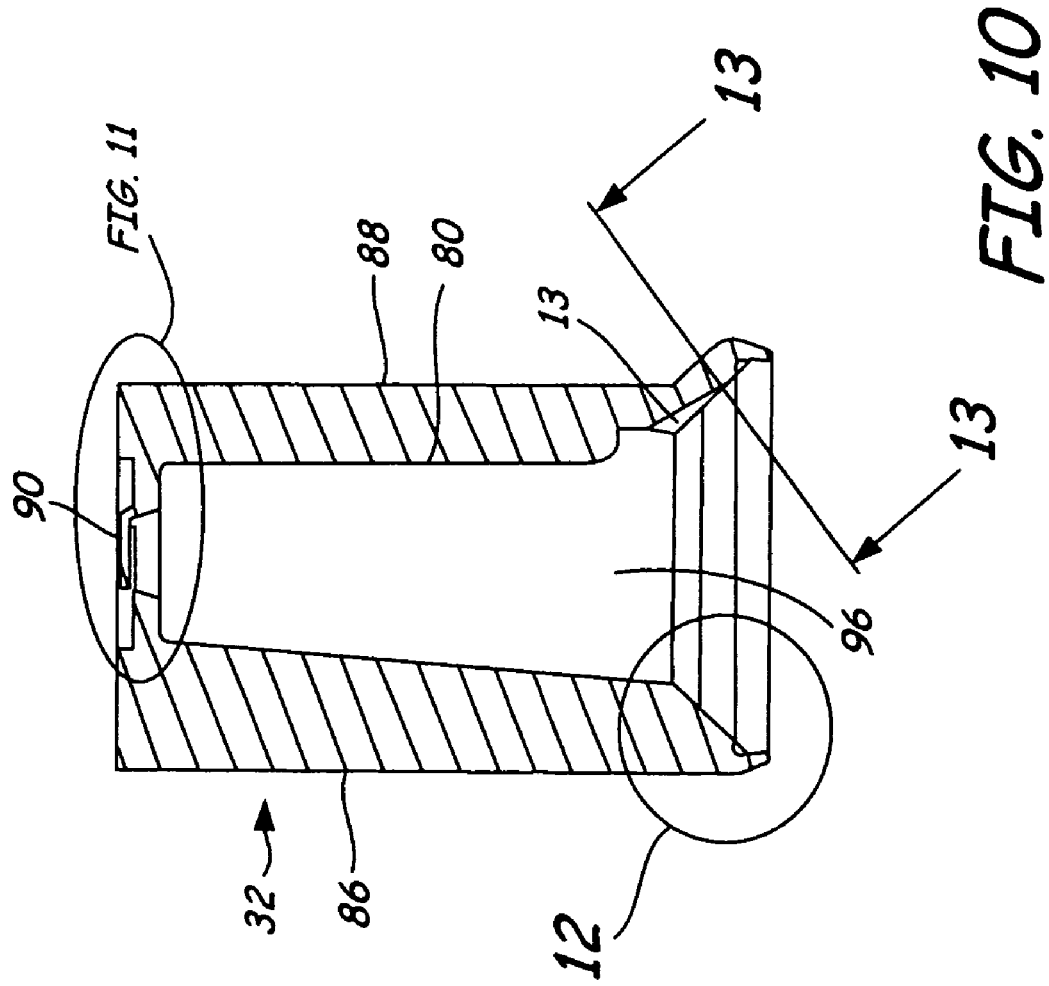
FIG. 10 is a cut-away view showing a partial cross-section of the impression cap.

FIG. 10 shows a cross-sectional view of the cap 32, wherein the internal flat 80 faces to the left. This figure provides a view of the geometry of the internal cavity 96. The positioning of the one way vent 90 and the secondary vent 13 are also shown.

Figure 11:
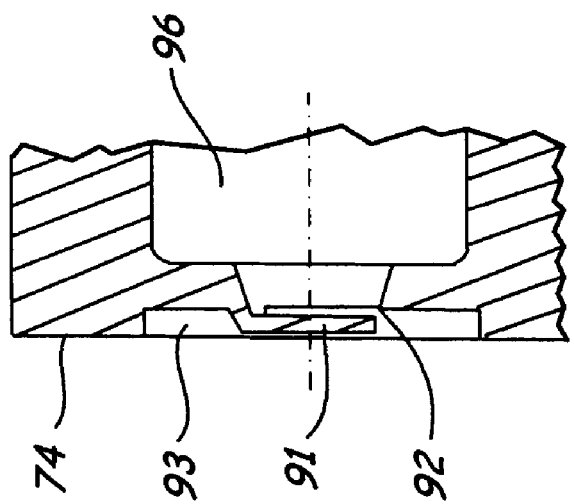
FIG. 11 is a detailed cut-away view showing a partial cross-section of a portion of FIG. 10, as indicated.
Figure 13:
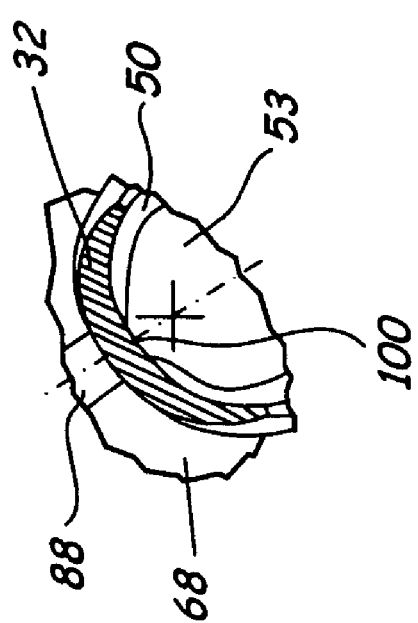
FIG. 13 is a detailed cut-away view showing a partial cross-section along lines 13—13 of FIG. 10.
Figure 12:
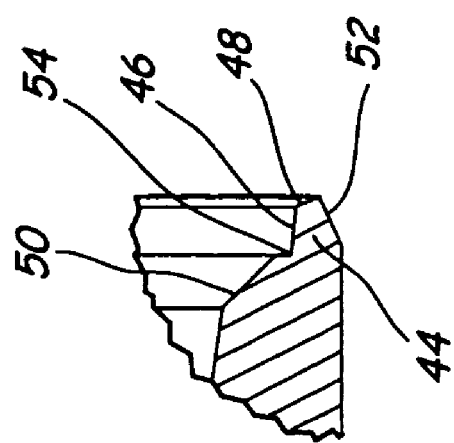
FIG. 12 is a detailed cut-away view showing a partial cross-section of a portion of FIG. 10, as indicated.

Certain portions, which are indicated in FIG. 10, are blown up and can be seen in FIGS. 11–13. FIG. 11 illustrates the one way vent 90 at the top of the cap 32 in a cross-sectional view. The vent 90 comprises a cover 91 attached to the top of the cap 32 via an attachment piece 89 and a gap 92 to release the air, as described above. It is the cover 91 which is pushed down by the impression material to seal the gap 92. A recess 93 may also be formed to keep the top surface of the cover 91 at, or below, surface 74.

Figure 15:
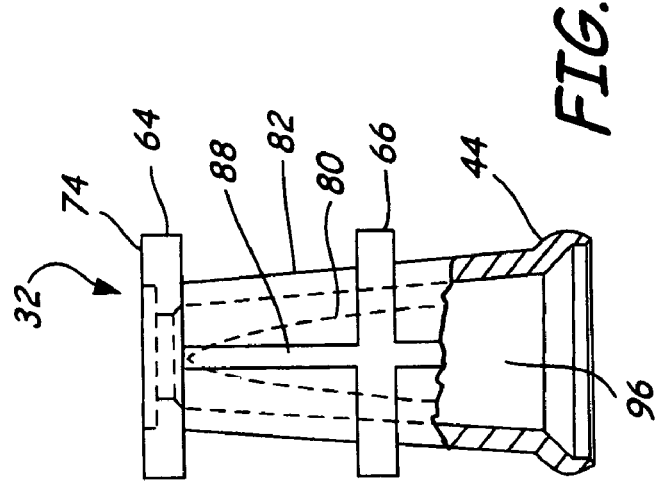
FIG. 15 is a partial cross-sectional view of the impression cap with phantom lines.
Figure 14:
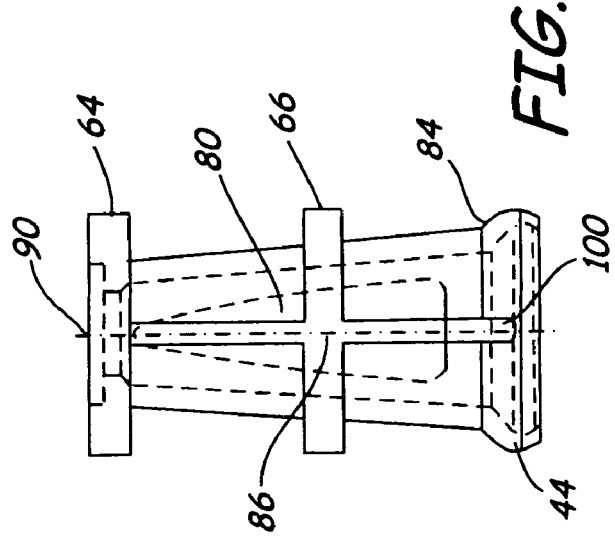
FIG. 14 is side view of the impression cap with phantom lines.
Figure 17:
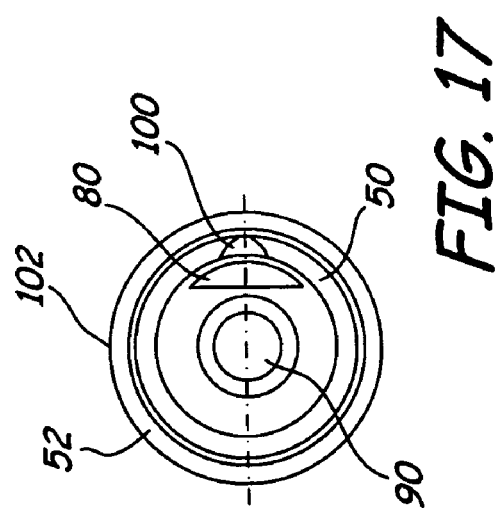
FIG. 17 is a bottom view of the impression cap.
Figure 16:
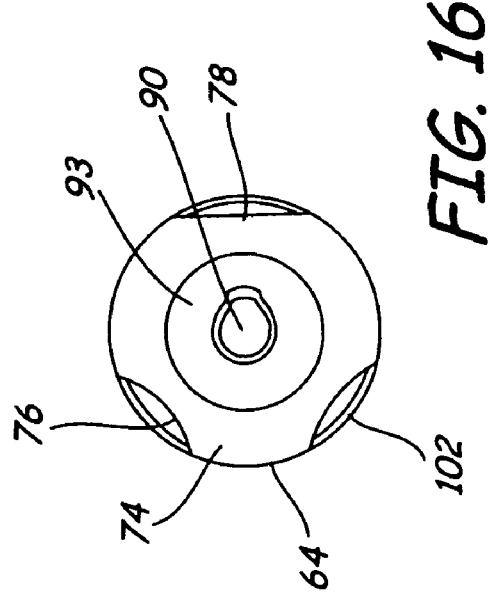
FIG. 16 is a top view of the impression cap.

FIG. 12 shows a cross-sectional view of the flange 44 portion of the cap 32. The portions numerically indicated are described above. FIG. 13 shows a cross-sectional view along the line 13—13 shown in FIG. 10. Similarly, the portions numerically indicated are described above. In this figure, a cross-section of the cap material 32 is shown FIGS. 14–17 show the cap 32 from different angles. The portions numerically indicated are described above. FIG. 14 is a view of the cap 32, wherein the vertical rib 86 is centered in the front. The inner rear surfaces are shown in phantom. FIG. 15 is a view of the cap 32, wherein the vertical rib 88 is centered in the front. The figure is a partial cross-sectional view and the remaining inner rear surfaces are shown in phantom. FIG. 16 is a top view of the cap 32 and FIG. 17 is a bottom view of the cap 32.

Figure 19:
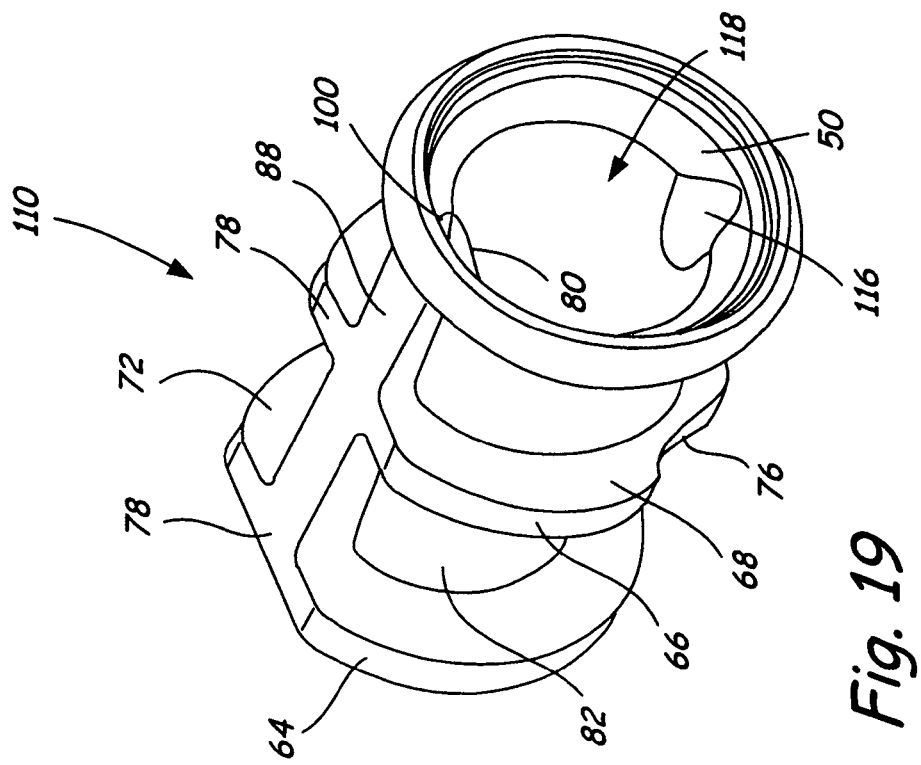
FIG. 19 is a view of the alternative embodiment of the impression cap.
Figure 18:
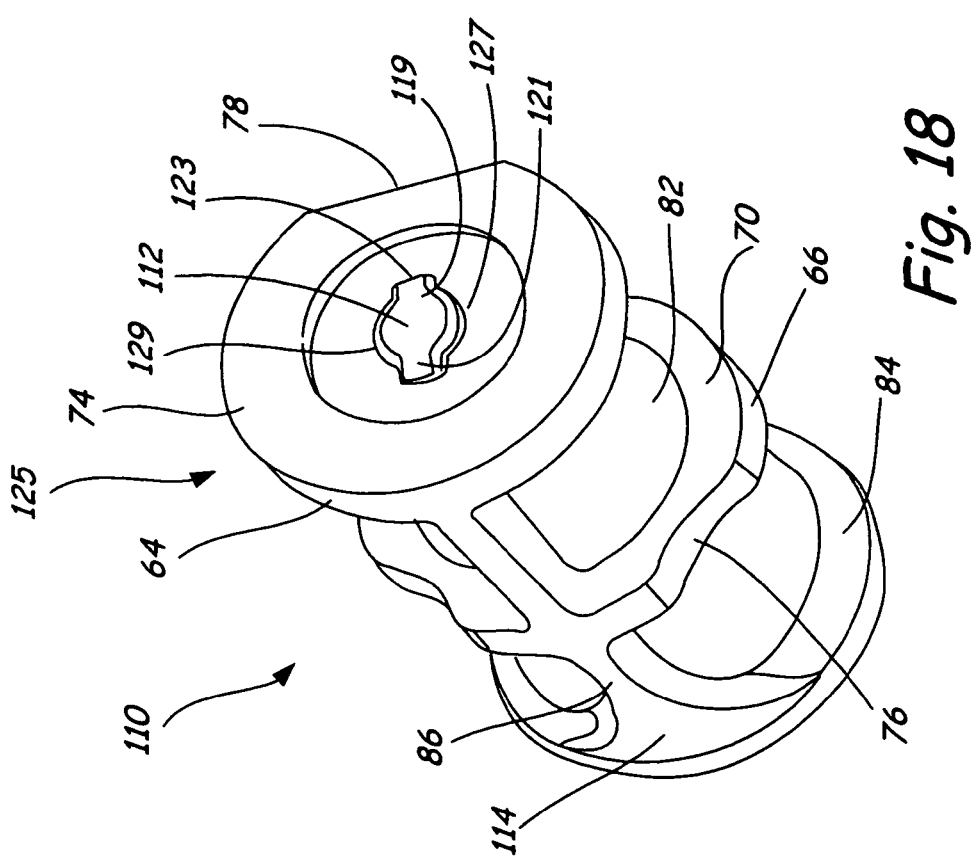
FIG. 18 is a view of an alternative embodiment of the impression cap.

FIGS. 18–19 show a further embodiment, identified as 110, of the impression cap. Cap 110 is similar to cap 32, but it has certain differences which may be added individually. As such, similar features are labeled similarly. Starting at the top of the cap 110, as shown in FIG. 18, the circumferential retention rib 64 has a flat indicator surface 78, but is free of recesses, as shown in FIG. 8 at 76, However, this embodiment does have recesses 76 in circumferential retention rib 66.

A further embodiment of the top vent 112 is also shown. This vent 112 will be shown and described in more detail in reference to later figures.

Also shown in FIG. 18 is a further alternative in the construction of vertical rib 86. In this embodiment, the bottom end 114 of rib 86 is flared. This extra mass in the bottom 114 of rib 86 aids in preventing cracking during the manufacturing of the cap. In this embodiment, the extra mass is positioned adjacent a second secondary vent, which is formed by a second channel 116. Second channel 116 is formed similarly to channel 100 and is used similarly for venting. The extra mass provided by bottom end 114 replaces the mass lost in forming channel 116. Although bottom end 114 is shown in a flared configuration, the present invention contemplates other configurations to increase the mass of rib 86 at the bottom, adjacent to the second channel 116.

FIG. 19 illustrates a view of the impression cap 110 from a further angle showing a portion of the internal geometry of the inner cavity 118. As with cap 32, the internal geometry of the impression cap 110 matches the geometry of the abutment/implant connection 31. In this figure, channel 116, which forms a second secondary vent 120 when the cap 110 is coupled with the abutment/implant assembly 31, can be seen. Secondary vents 13 and 120 are formed and work similarly.

Figure 20:
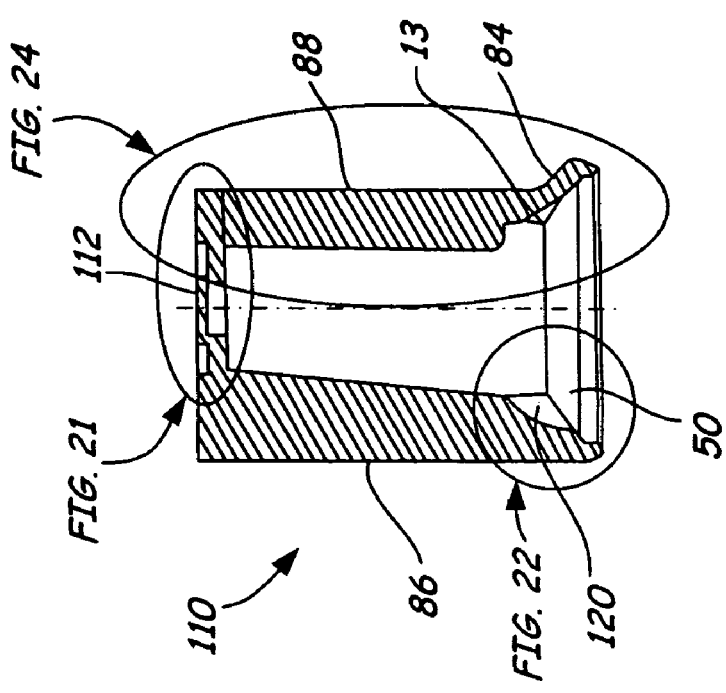
FIG. 20 is a cut-away view showing a partial cross-section of the alternative embodiment of the impression cap.

FIG. 20 shows a cross-sectional view of the cap 110, wherein the internal flat 80 faces to the left. This figure provides a view of the geometry of the internal cavity 96. The positioning of the one way vent 112 and the secondary vents 13, 120, are also shown.

Figure 21:
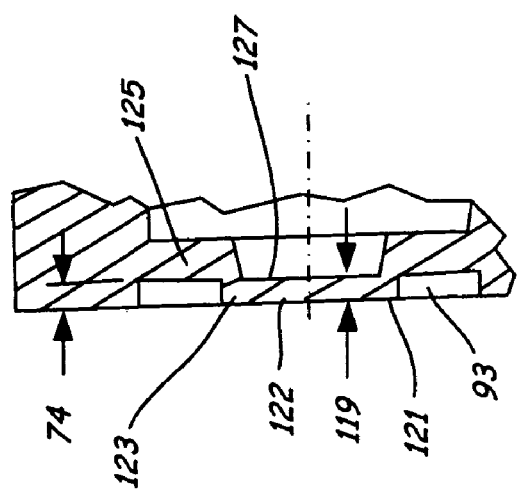
FIG. 21 is a detailed cut-away view showing a partial cross-section of a portion of FIG. 20, as indicated.
Figure 22:
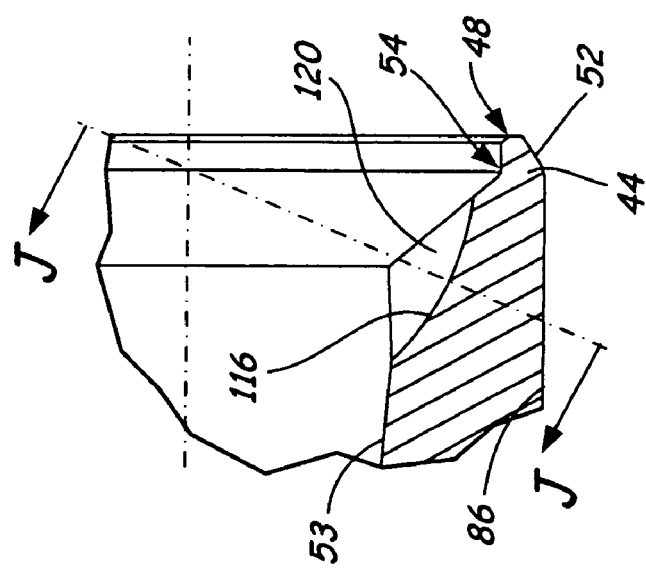
FIG. 22 is a detailed cut-away view showing a partial cross-section of a portion of FIG. 20, as indicated.
Figure 24A:
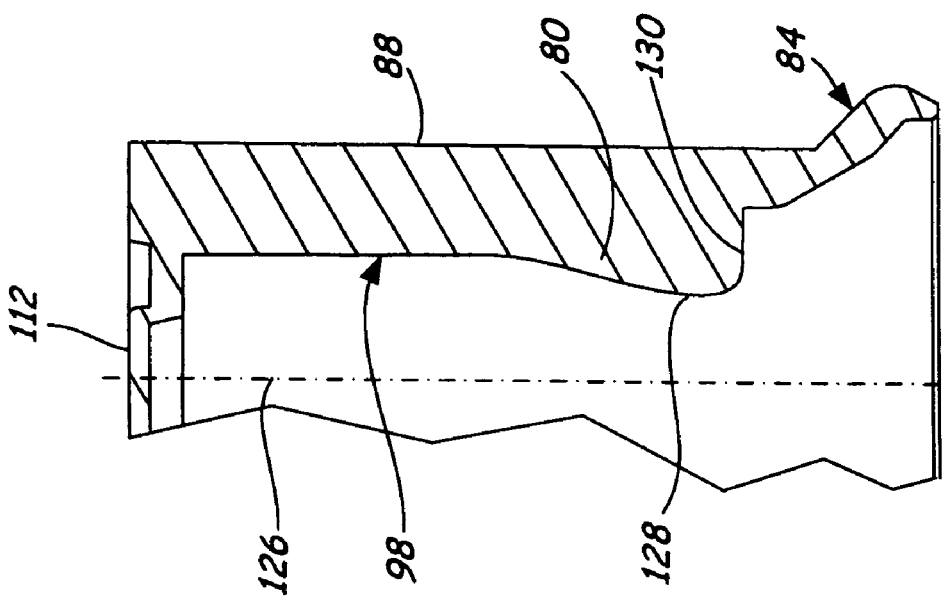
FIG. 24A is an exaggerated cut-away view showing a partial cross-section of an alternative embodiment of the impression cap.
Figure 24:
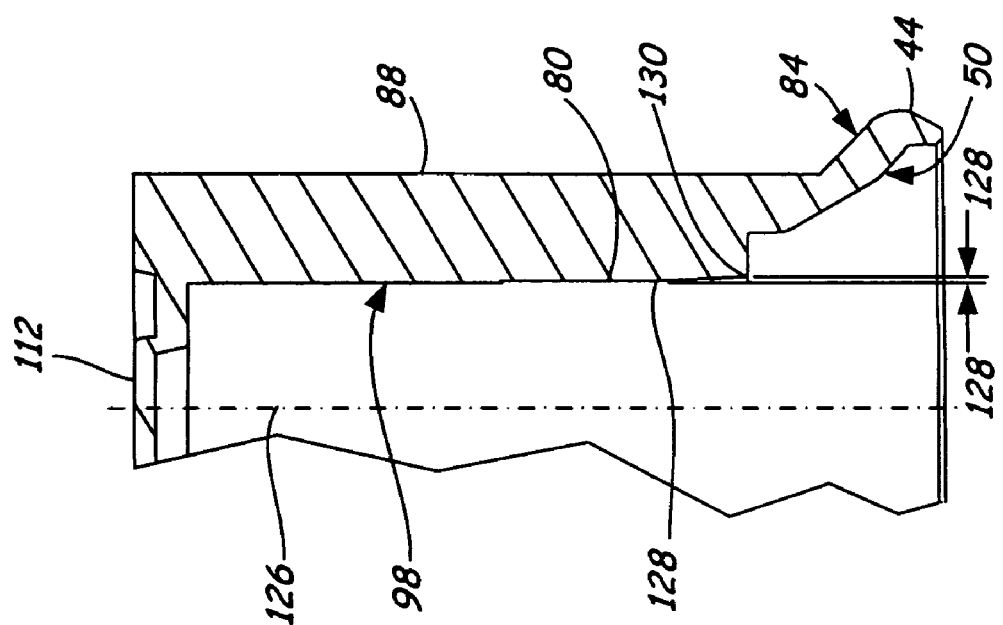
FIG. 24 is a detailed cut-away view showing a partial cross-section of a portion of FIG. 20, as indicated.

Certain portions, which are indicated in FIG. 20, are blown up and can be seen in FIGS. 21, 22 and 24. FIG. 21 is a blow-up of the encircled portion in FIG. 20 labeled "FIG. 21," and illustrates an alternative embodiment of the one way vent 112 at the top of the cap 110 in a cross-sectional view. The vent 112 comprises a cover 119, having fast and second attachment pieces 121, 123, which attach the cover 119 to the top 125 of the cap 110. On either side of the cover 119, there is a vent opening 127 and a vent opening 129 (shown in FIG. 18), to release air when the cap is placed over the abutment. As with vent 90, the air passages close when impression material is pressed over the cap. As with cap 32, a recess 93 may also be formed to keep the top surface of the cover 119 at, or below, surface 74.

FIG. 22 shows a cross-sectional view of the flange 44 portion of the cap 110, indicated as "FIG. 22" in FIG. 20. The cross-section is through second vent 120. The portions numerically indicated are described above.

Figure 23:
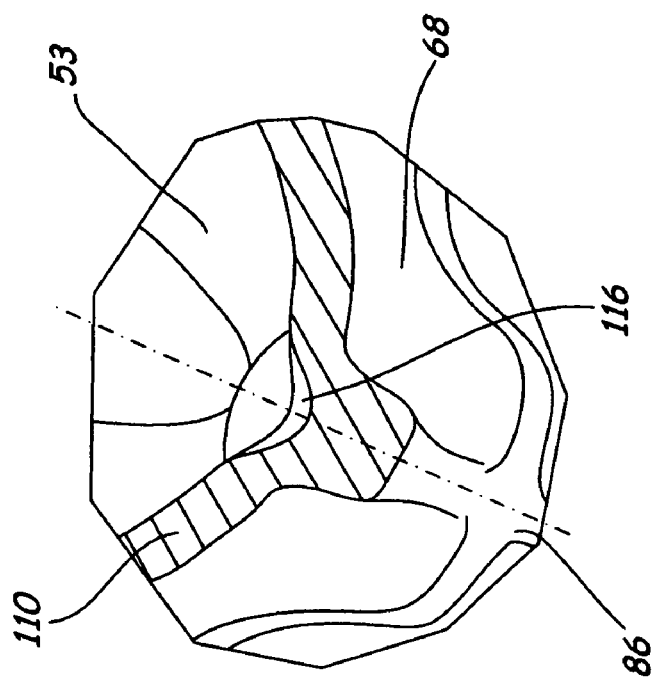
FIG. 23 is a detailed cut-away view showing a partial cross-section along lines J—J of FIG. 22.

FIG. 23 shows a cross-sectional view of the flange 44 portion of the cap 110, indicated as J—J in FIG. 22. 110 indicates the cap material. The portions numerically indicated are described above.

FIG. 24 shows a cross-sectional view of a portion of the cap 110, indicated as "FIG. 24" in FIG. 20. The cross-section is through abutment flat 80, perpendicular to the abutment surface 98. The portions numerically indicated are described above.

An additional individual feature may also be seen in this figure. In this embodiment, instead of the surface 98 of the abutment flat 80 being parallel with, or slightly angling away from, the center line 126, as shown in the other embodiments, a portion of the surface 98 angles toward the center line 126 forming a bulge 128. An exaggerated view of bulge 128 may be seen in FIG. 24a. The bulge 128 may be positioned at other places along the surface 98. In the embodiment shown, the bulge 128 is positioned on the lower part of the flat 80. Eventually, the surface 98 angles back away 130 from the center line 126. This bulge 128 or extension inward provides an alternative or additional press fit mechanism that provides an increase in rotational and vertical stability. The feature 128 also accounts for manufacturing tolerance by compressing the bulge 128 against the flat 80. It removes the necessity of having an exact fit between the internal geometry of the impression cap and the outer geometry of the abutment and the circumferential flange 44 and the collar 16 of the implant 10.

Figure 26:
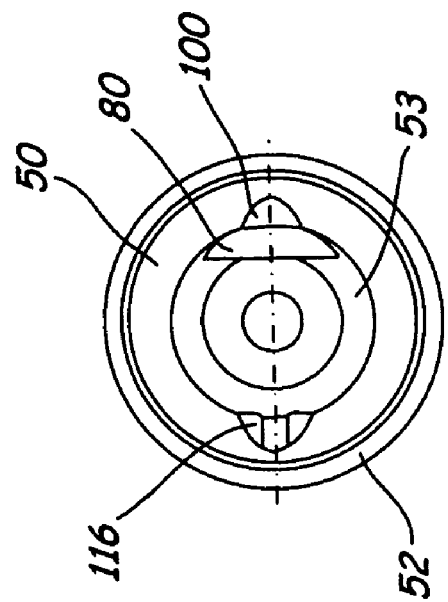
FIG. 26 is a bottom view of the alternative embodiment of the impression cap.
Figure 25:
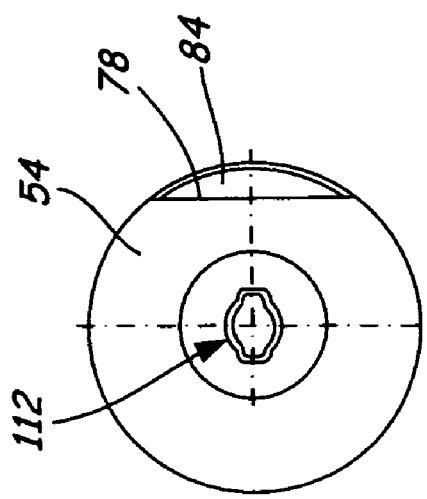
FIG. 25 is a top view of the alternative embodiment of the impression cap.

FIGS. 25 and 26 are views of the cap 110 from the top and bottom, respectively. The portions numerically indicated are described above.

Figure 28:
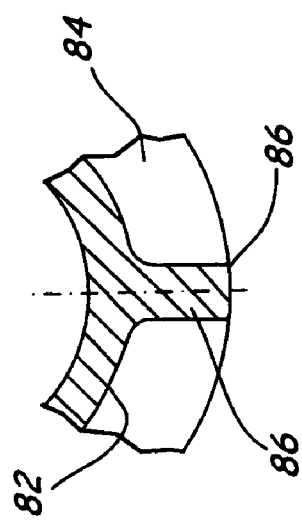
FIG. 28 is a detailed cut-away view showing a partial cross-section along lines H—H of FIG. 27.
Figure 27:
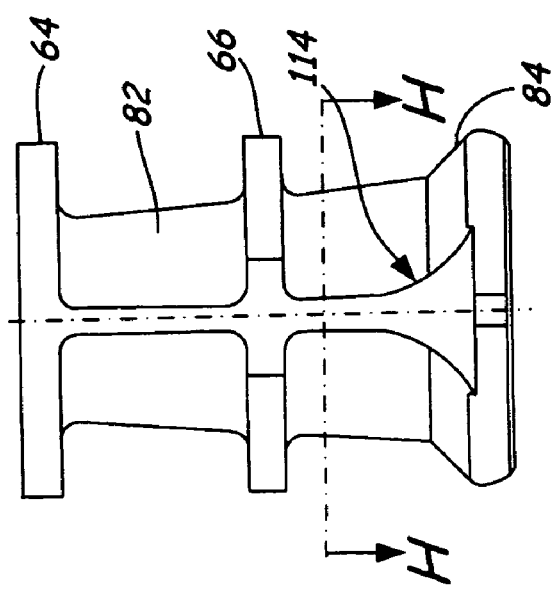
FIG. 27 is side view of the alternative embodiment of the impression cap shown in FIG. 25.

FIG. 27 is a side view of cap 110 with rib 86 in the front. FIG. 28 is a cross-sectional view of a portion of FIG. 27, indicated as H—H. The portions numerically indicated are described above.

Figure 30:
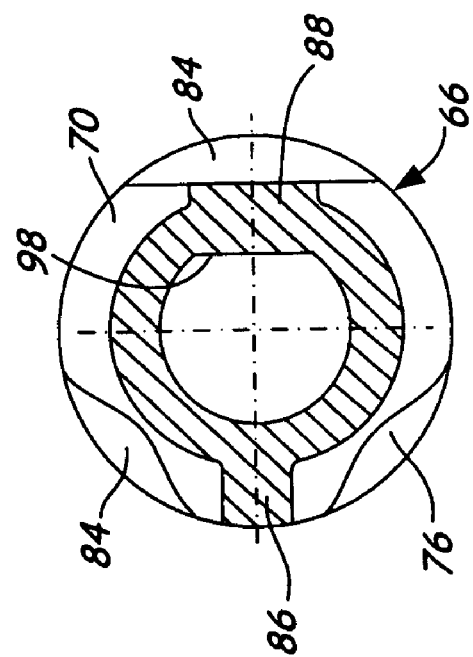
FIG. 30 is a detailed cut-away view showing a partial cross-section along lines G—G of FIG. 29.
Figure 29:
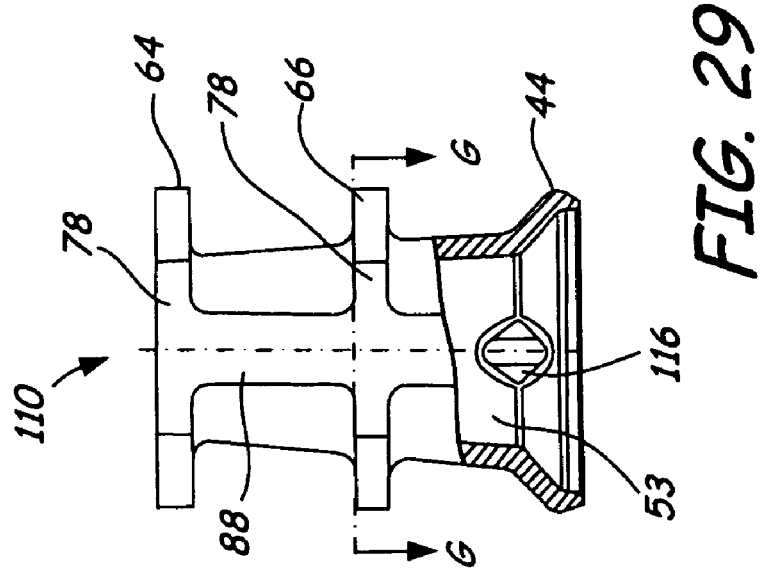
FIG. 29 is a partial cross-sectional view of the alternative embodiment of the impression cap.

FIG. 29 is a view of the cap 110, wherein the vertical rib 88 is centered in the front. The lower portion of the cap 110 is cut away to reveal the channel 116. FIG. 30 is a cross-sectional view of a portion of FIG. 29, indicated as G—G. Rib 88 is shown as being wider than rib 86 so as to support the internal flat 80 geometry. It is also seen as shallower than rib 86 due to the indicator flat surface 78. The portions numerically indicated are described above.

Figure 31:
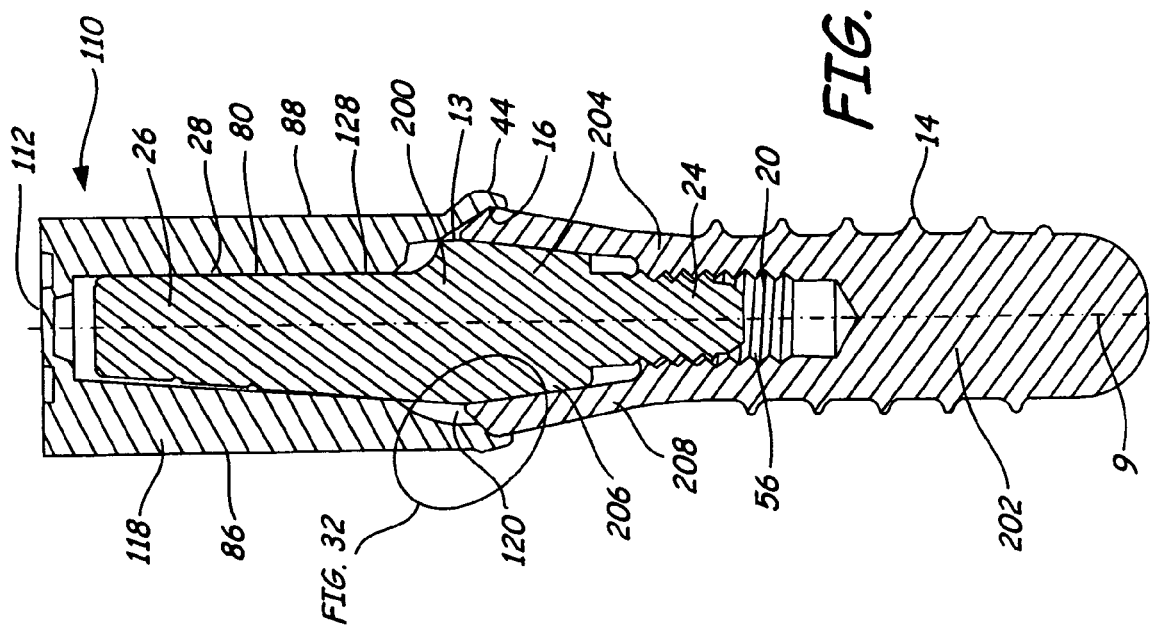
FIG. 31 is a cut-away view showing a partial cross-section of an implant/abutment assembly and an impression cap mounted thereon.
Figure 33:
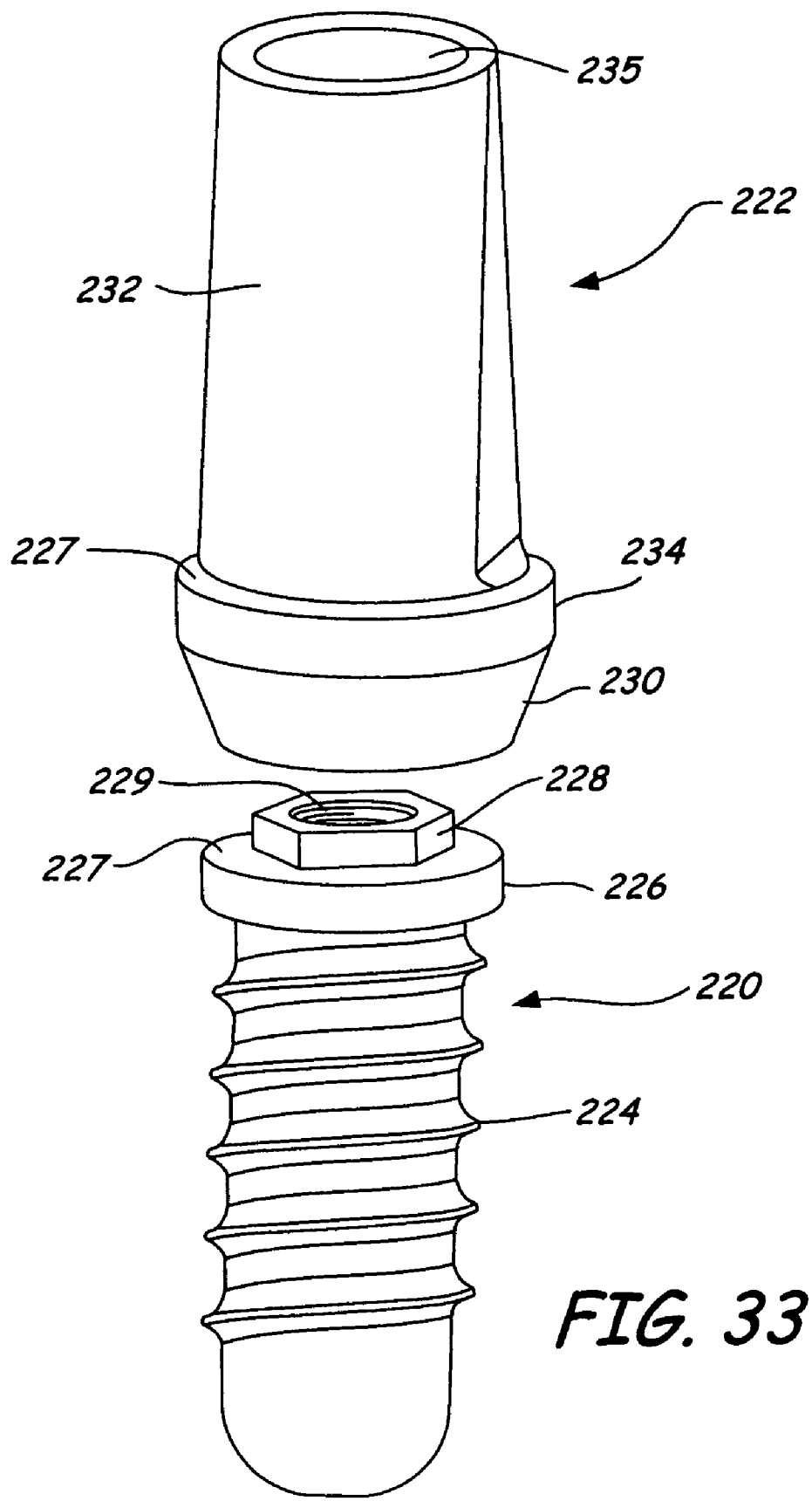
FIG. 33 is an isometric view of a two-stage dental implant and an extension abutment, according to one embodiment of the present invention.

Similar to FIGS. 6–7, FIG. 31 illustrates a cross-sectional view of an embodiment of an impression cap 110 position on an abutment 200, which is in turn inserted in an implant 202. The device is positioned to view the abutment flat 28 from the side such that the cross section is through the first 13 and second 120 secondary vents. This particular embodiment incorporates the bulge 128 feature and uses cap 110, which may accommodate a situation where the internal geometry of the cap 110 is not an exact fit with the external geometry of the abutment, as shown.

In these figures, the impression cap 110 is positioned on an abutment post 26 of an abutment 200, which is screwed into an implant 202 to illustrate the fit between the impression cap 110 and the abutment/implant assembly 204, as well as the fit between the abutment 200 and the implant 202. This particular embodiment illustrates a slightly different abutment/implant assembly 204. This particular embodiment utilizes a conical mating system for a secure and stable fit between the abutment 200 and the implant 202. This mating system differs from the system shown in FIGS. 6–7 in one respect in that it does not include the stepped feature 60, 62. The mating system shown in FIG. 31 utilizes a conical male portion 206 of the abutment 200 which fits into a conical female portion 208 of the implant 202.

Figure 32:
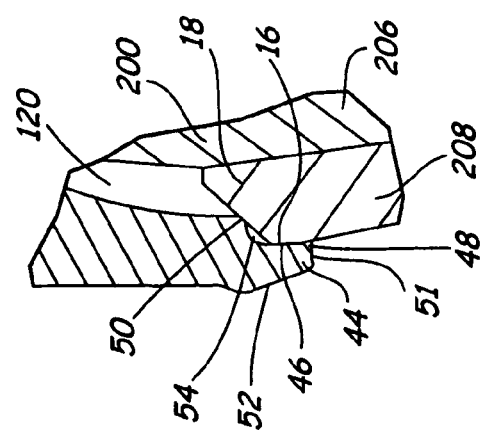
FIG. 32 is a detailed cut-away view showing a partial cross-section of a portion of FIG. 31, as indicated.

FIG. 32 is a blown-up view of a portion of FIG. 31, as indicated by the encircled portion labeled "FIG. 32," in FIG. 31. The cross-section portion is through the second secondary vent 120. The figure also illustrates the engagement between the press fit mechanism of the impression cap 110 and the implant 202. This engagement occurs primarily between the peripheral portions of the collar 16 of the implant 202 and the engagement end or press fit mechanism of the impression cap 110. As mentioned above, the press fit or friction fit of the impression cap is produced by the press fit mechanism of the cap. The mechanism provides an inwardly directed radial force against the periphery of the collar.

As shown in FIG. 32, at the engagement end, the press fit mechanism of the impression cap 110 has a circumferential flange 44 to guide the engagement end of the impression cap 110 over the collar 16 of the implant 202. The flange 44 has a press or squeeze surface 46 which is substantially parallel with the axis 9 of the implant 202 and press fits to the maximum diameter of implant collar 16. The connection between the flange 44 and the collar 16 is a pressure frictional fit, wherein the flange 44 squeezes the outer surface of the collar 16. The outer surface of the collar 16 which contacts the flange 44 may be flat to provide a greater contact surface.

The flange 44 further includes a lead in taper 48 to guide the flange 44 over the collar 16. During assembly of impression cap 110 onto implant 202, taper 48 contacts the outer surface of the implant collar 16 first. The taper 48 helps expand the impression cap 110 so that pressing surface 46 can press fit (or friction fit) to the maximum diameter of implant collar 16. The lead in taper 48 can be a chamfer, radius, or the like.

The flange 44 may have an extra surface 51 between angled surface 52 and surface 48 to provide a blunt end to the flange 44. Surface 51 may be substantially perpendicular to pressing surface 46 or rounded.

The impression cap 110 also comprises an angled surface 50 which provides a reference stop with the shoulder 18 of the implant 202, as described above. Surface 50 is only partially shown in these figures because the cross-section is through the secondary vents.

The flange 44 further includes angled surface 52 formed by its exterior. This surface 52 retracts the gingival tissue away from the implant table. This allows the impression cap 110 to automatically capture the implant margin, or collar 16. This also eliminates the need to pack cord, a common but tedious dental procedure.

As with the above described embodiment, the engagement end of the impression cap 110 also forms a curved relief 54 between angled surface 50 and the body of the flange 44. This relief 54 removes the acute angle formed between the pressing surface 46 and the angled or stop surface 50. The curved relief 54 removes any stress risers that may occur within the material during assembly as the lead in taper 48 moves over the implant collar.

FIGS. 31 and 32 further show the fit between the abutment 200 and the implant 202. The implant 202 has a bored hole 20, which is partially threaded 56 and partially conical 208. These portions receive threaded portion 24 and conical portion 206 of the abutment 200 for a secure fit.

FIGS. 33, 34, 35A, and 35B show various views of a two-stage dental implant 220 and an extension abutment 222. As shown, the implant 220 includes a threaded portion 224 and a head 226. In the embodiment shown, the head 226 includes a hex support 228. The implant 220 further includes an internally threaded longitudinal bore 229 extending through the hex support 228 and into the implant 220. The extension abutment 222 includes a base or cuff 230 and an abutment post 232, together defining a shoulder 227. A collar 234 extends around a periphery of a top portion of the cuff 230 to define a retention edge. In addition to the structure shown in FIG. 33, the cuff 230 and the collar 234 may include an outer surface that widens conically upwardly similar to or identical to the surface 17 (FIG. 7A) and the collar 16 (FIG. 1) of the dental implant head 12.

The extension abutment 222 includes an upper bore 235 and a lower bore 236 extending longitudinally through its center and a retaining shoulder 237 between the bores 234 and 235. In the embodiment shown, the engagement end of the cuff 234 includes a hex-shaped recess 221 adapted to mate with the hex support 228 of the head 226. The mating of the hex-shaped recess 221 and the hex support 228 prevents rotational motion of the extension abutment 222 with respect to the implant 220. When the abutment 222 is installed onto the implant 220, an implant/abutment screw (not shown) engages the shoulder 237 and is threadly received by the threaded bore 229.

Figure 34:
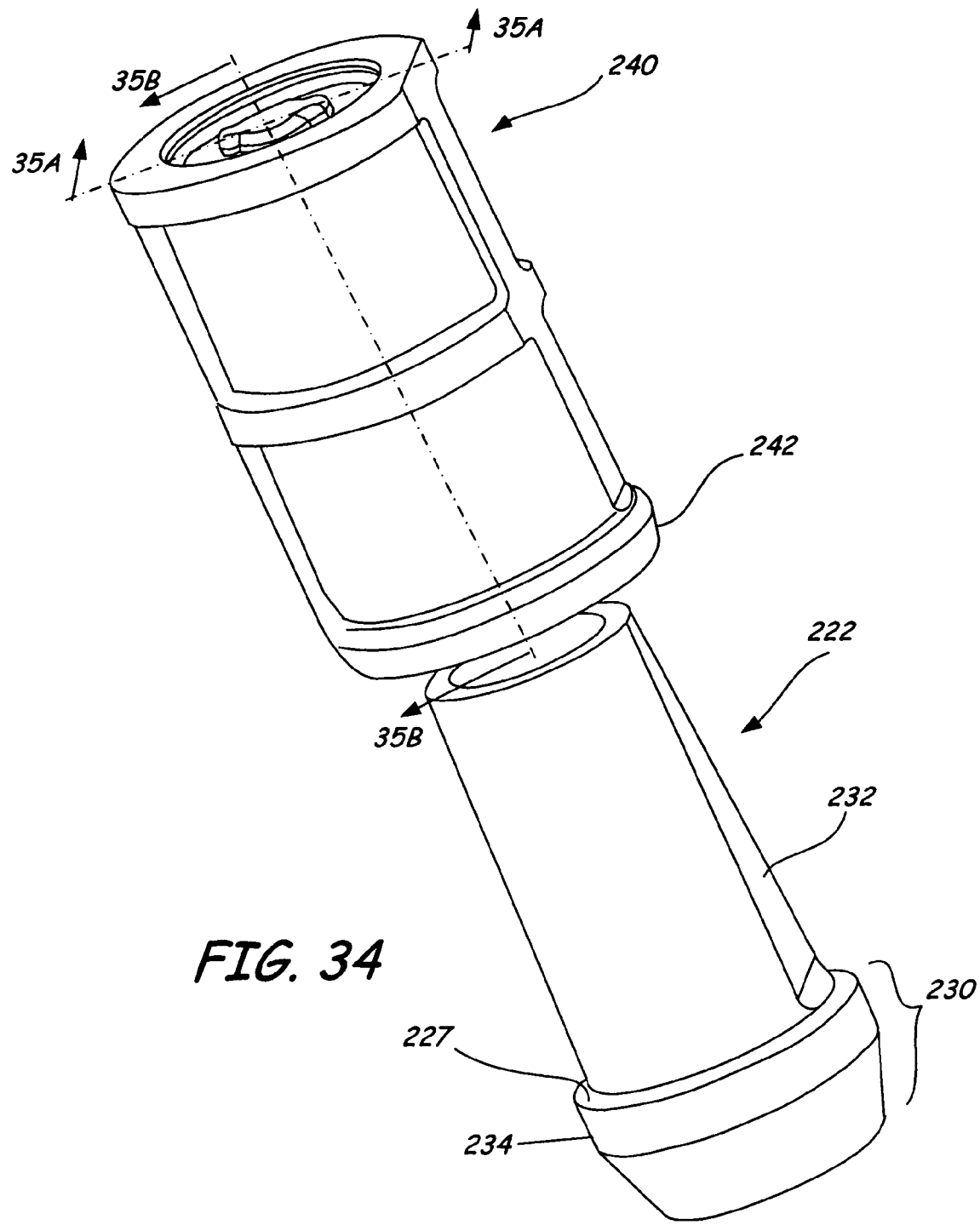
FIG. 34 is an isometric view of the extension abutment of FIG. 33 and an impression cap adapted for mounting over the extension abutment.

FIG. 34 is an isometric view of the extension abutment 222 and an impression cap 240. The impression cap 240 shown in FIG. 34 may have a structure similar or identical to the structure of the impression cap 32 or the impression cap 110. Like the impression cap 32 of FIG. 2 and the impression cap 110 of FIG. 18 described above, the impression cap 240 has a hollow interior geometry having portions that generally mate with corresponding surfaces of the abutment 232. Also, like the impression cap 32, the impression cap 240 includes a contoured retention geometry to stabilize the impression cap 240 within the impression material. The impression cap 240 also has a retaining flange 242 adapted to guide the impression cap 240 over the collar 234 of the abutment 222 and to retain the cap 240 relative to the abutment 222 when so installed.

Like the cap retaining structure of the impression cap 32, shown in FIGS. 7 and 7A, the flange 242 is sized and configured to form a friction or interference fit with the outer surface of the collar 234 and more specifically, a retaining edge or edge portion of the collar 234. This interference fit should be sufficient to retain the impression cap 32 on the abutment 222 and to prevent inadvertent displacement or removal during the application of the impression molding material and creation of the impression mold. Thus, the inner diameter of the flange 242 must be equal to or less than the outer diameter of the collar 234. To achieve this retaining force, the inner diametrical dimension of the flange 242 is, in one embodiment, about 0.004 inches to about 0.008 inches less than the outer diametrical dimension of the edge portion of the collar 234, which is equivalent to an interference dimension, between the flange 242 and the collar 234, of about 0.002 inches to about 0.004 inches. In another embodiment, this interference dimension is about 0.0025 inches to about 0.0035 inches. In general, the geometrical and dimensional relationships between the impression cap 32 and implant 10 of FIG. 1 is the same as that between the impression cap 240 and the abutment 222 of FIG. 34. Thus, the flange 242 comprises a structure substantially the same as the flange 44 of FIGS. 7 and 7A including the surfaces 46, 48, 51, and 52. The impression cap 240 further includes an inner angled surface or inner shoulder 225 adapted to mate with the outer shoulder 227 of the extension abutment 222.

When the implant 220 is placed in the underlying bone structure, the threaded portion 224 extends into the bone and the head 226 seats against the outer surface of the bone. The extension abutment 222 is then secured to the implant 220 using an abutment screw or bolt (not shown) extending through the extension abutment bores 235 and 236 and into the implant 220. In one embodiment, a hex-shaped recess 221 (shown in FIGS. 35A and 35B) in the extension abutment 222 is mated with the hex support 228 to prevent rotation of the extension abutment 222 with respect to the hex support 228. The extension abutment 222 has a cuff 230 having a length that extends slightly above the level of the gingiva. Extension abutments 222 of various lengths can be provided to allow the dentist or surgeon to select the extension abutment 222 having the appropriate length for the patient's mouth.

Figure 35B:
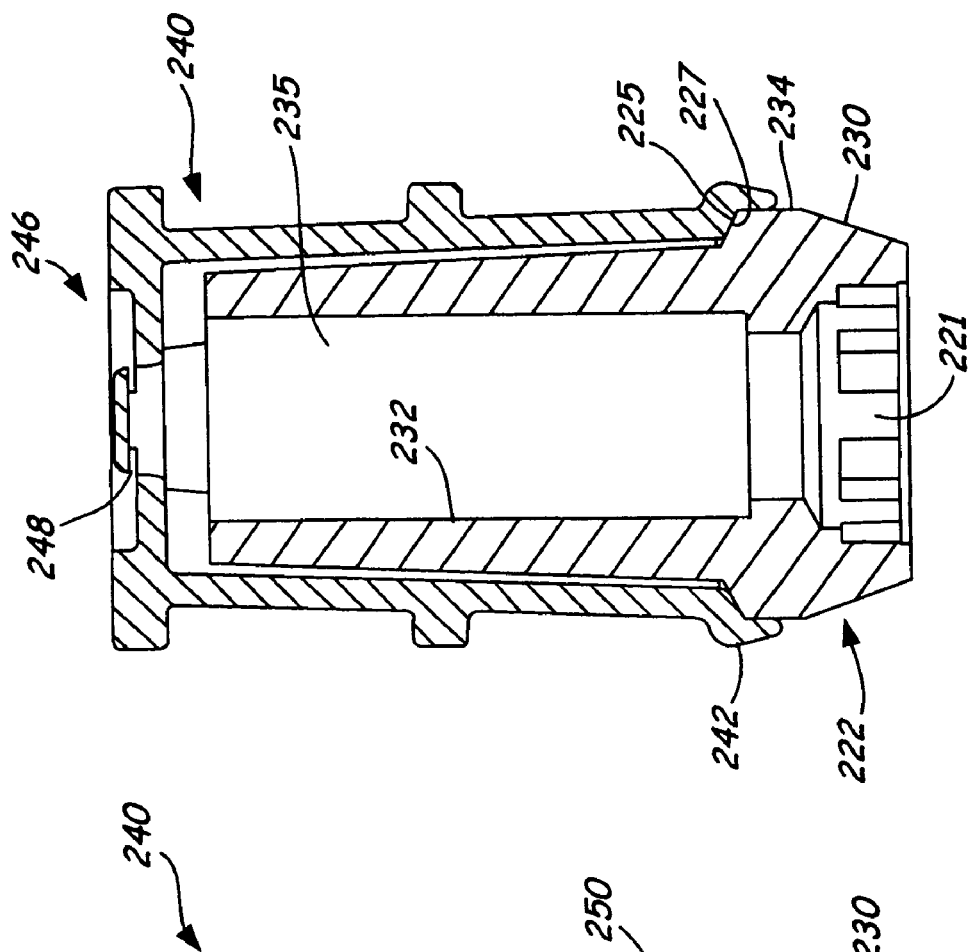
FIGS. 35A and 35B are cross-sectional views (oriented at 90 degrees relative to one another) of the impression cap, taken along the lines 35A—35A and 35B—35B in FIG. 34, respectively.
Figure 35A:
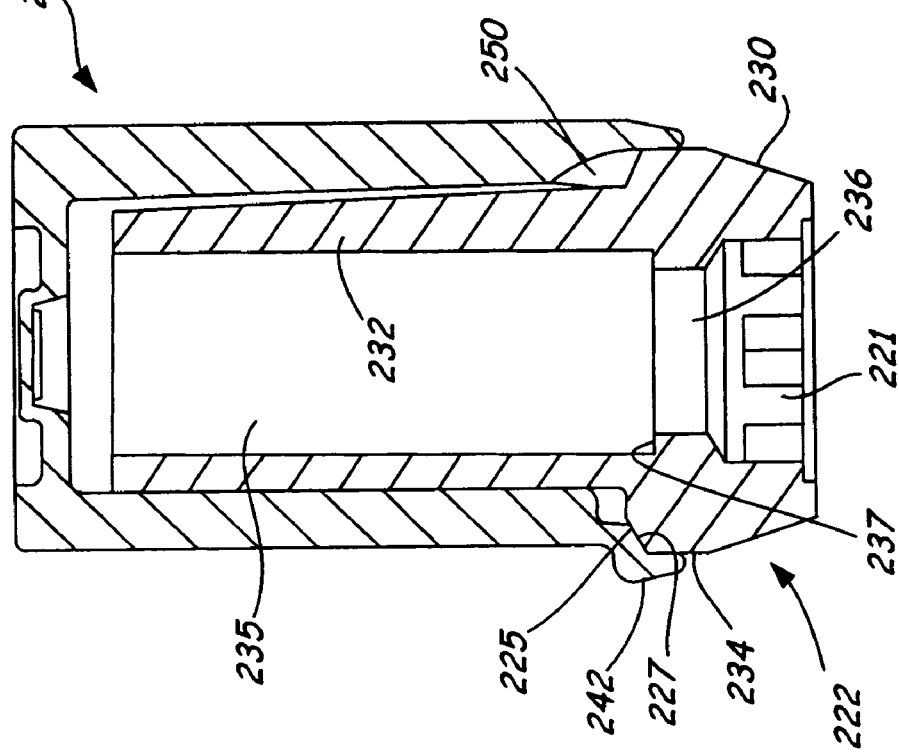

To install the impression cap 240, the cap 240 is aligned with, and pressed onto, the extension abutment 222. FIGS. 35A and 35B show cross-sectional views of the impression cap 240 fully seated on the extension abutment 222. During installation of the impression cap 240 on the extension abutment 222, the flange 242 contacts and extends over the cuff 230 to form a friction or interference fit and the angled surface 225 of the cap seats against the angled surface or outer shoulder 227 of the abutment 222. The impression cap 240 is coupled to the collar 234 of the extension abutment 222 by the friction between the outer surface or retention edge of the collar 234 and the inner surface of the flange 242. As discussed above, the diameters and geometry of the collar 234 and the flange 242 determine the tightness of the interference fit.

As shown, the collar 234 comprises a generally cylindrical configuration defining the outermost diametrical dimension of the abutment 222 and, unlike the retention surface 47 of FIG. 7A, is longer in a direction parallel to the axis 9, than the inner surface of the flange 242. The length of the collar 234 could, however, be shorter, similar to the collar 16 and edge 47 of FIG. 7A. As further shown in FIG. 35B, the impression cap 240, includes a one-way vent 246 having an air gap 248, which allows air to escape from the internal cavity of the impression cap 240 during engagement with the abutment 222. As shown in FIG. 35A, the impression cap 240 also includes a secondary vent 250 located on a lower portion of the impression cap 240 and the retaining flange 242. The secondary vent 250 also acts to allow air to escape from the internal cavity of the impression cap 240 during engagement with the abutment 222.

The impression cap embodiments are made from any material compatible with dental usage and the impressing process. Suitably the material is an elastic or moldable material, including, but not limited to, thermoplastic materials, such as polypropylene, polyethylene, acetal (i.e., Delrin or Celcon), HDPE, PEEK, PEAK, or Thermoset. An elastic material is advantageous to provide sufficient squeezing force between the impression cap and the implant collar 16. The press/friction fit combined with the squeezing force provided by the elastic material provides sufficient retention of the impression cap to the implant.

On occasion, the dentist or orthodontic surgeon placing the abutment 22 (in a single-stage system) or the extension abutment 222 (in a two-stage implant system) determines that the height or shape (or both) of the abutment post 26 or the abutment post 232 requires modification. For example, the dentist may decide that the abutment post 26 extends too high within the mouth of the patient with respect to surrounding teeth. Or, for example, the dentist may decide that one side of the abutment post 26 extends too close to the outer surface of the prospective crown. In this situation, the dentist may modify the shape of the abutment post 26 by removing (through grinding or the like) one or more portions. If the dentist modifies the size or shape of the abutment post 26, information relating to the modification must be communicated to the lab, which creates the model of the patients teeth.

FIG. 36 is a flowchart showing a process for communicating this reduction of the size or shape of the abutment post 26. As shown in FIG. 36, in one embodiment, after reducing the size of the abutment post 26 (step 260), the dentist installs a modification cap, in the form of a first impression cap or other structure, over the abutment post 26 and onto the implant 10 (or an extension abutment 222), as described above, such that a friction or interference fit is created between the modification cap and the implant 10 (step 262). Although in one embodiment of the process the modification cap is an impression cap similar to those used in the impression process, the modification cap may include other structures as long as the interior size and configuration, and the retaining means, of the other structure is the same as or substantially the same as the impression cap being used in the impression process. The dentist then removes portions of this installed modification cap, such that it matches all newly-formed surfaces resulting from the reduction of the abutment post 26 (step 264). For example, if the height of the abutment post 26 was reduced, then the top of the modification cap is removed down to the new reduced height of the abutment post 26.

After the modification cap is modified to match the reduction in size of the abutment post 26, the modified or reduced modification cap is removed and replaced by an impression cap as described above and shown by reference characters 32, 110, or 240. The dentist then creates a negative 36 (shown in FIG. 4) from impression material 34 according to an impression process, as described above (step 266). The negative 36 and the modified or reduced modification cap are then sent to a lab for creation of a stone model of the patient's teeth, using the steps set forth above (step 268). After the lab creates the stone model, the modified or reduced modification cap is placed onto the abutment post of the analog on the stone model, and the abutment post is reduced to match the modified or reduced modification cap. When this is done, the modified abutment post of the analog in the stone model replicates the modified abutment post present in the patient's mouth (step 270).

Accordingly, an aspect of the present invention is a method of reducing an abutment post and communicating that reduction information to a lab, which includes the steps of providing an abutment and a corresponding modification cap having an interior substantially matching an exterior portion of such abutment. The abutment is then installed and reduced or modified where necessary. Following such reduction or modification, the modification cap is installed onto the implant/abutment or abutment. Such installed modification cap is then modified so that it matches the previously reduced or modified abutment. If desired, the abutment and the modification cap can be modified or reduced at the same time. This modified modification cap is then removed and an impression cap is installed onto the implant/abutment or onto the abutment. An impression is then taken. After curing, the impression material, with the second impression cap embedded therein, is removed from the patient's mouth and transferred to the lab along with the modified modification cap. After the stone model is created in accordance with conventional procedures, the lab technician installs the modified modification cap into the abutment of the analog and reduces such abutment post to match the modified modification cap. The lab then creates the crown or replacement tooth to match the modified abutment post of the analog and delivers the crown or replacement tooth to the dentist. Thus, the crown or replacement tooth that is delivered to the dentist for installation exactly matches the reduced or modified abutment post in the patient's mouth.

In some circumstances, the lab, after having created the stone model replicating the situation in the patient's mouth, may decide that the abutment requires further modification. For example, the lab may determine that a replacement tooth or crown cannot be properly attached without reducing the height of the abutment. In this situation, the reduction coping technique shown in FIG. 36 can be used in reverse. In other words, the lab can reduce the size of the analog abutment post as needed and then install a modification cap and reduce it to match the reduced abutment. The lab can then send this modified modification cap back to the dentist, along with the replacement tooth or crown. The dentist then reduces the size of the abutment in the patient's mouth, using the modified modification cap as a pattern or template. The size of the abutment may be reduced using a carbide or diamond bur and copious irrigation.

Figure 37A:
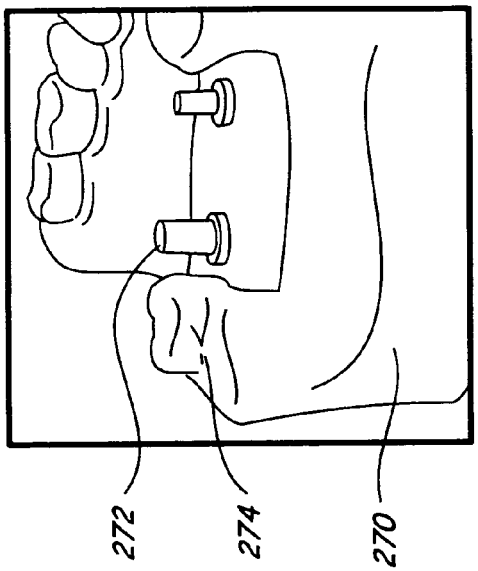
FIGS. 37A–37F are diagrams showing a process for performing reduction of an abutment in a stone model and a corresponding reduction to an abutment in a patient's mouth, according to one embodiment of the present invention.
Figure 37B:
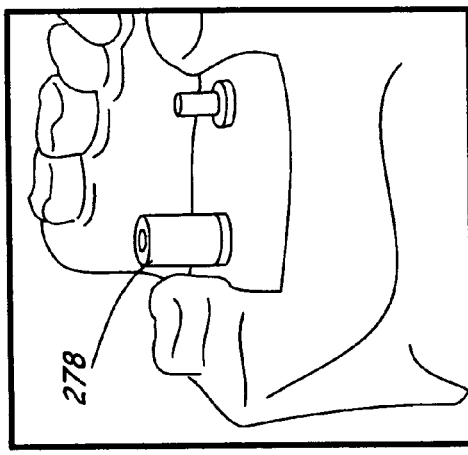
Figure 37C:
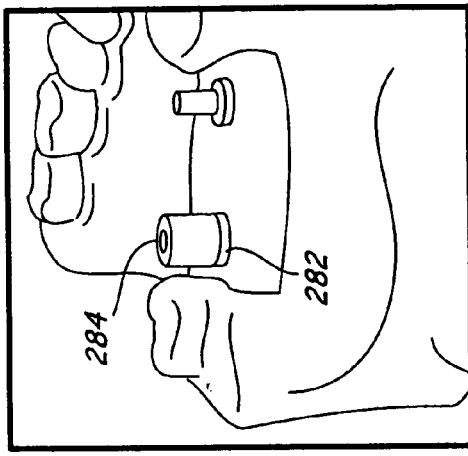
Figure 37D:
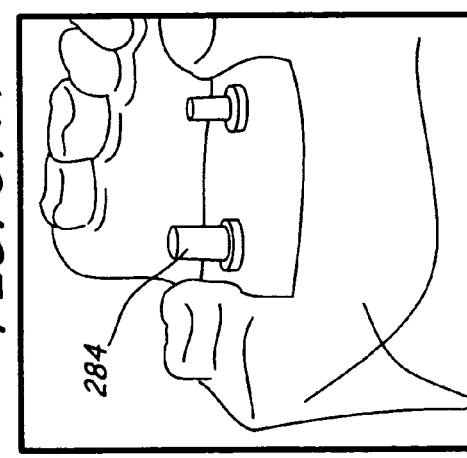

FIGS. 37A–F illustrate one embodiment of this reduction coping technique. FIG. 37A shows a stone model 270 including an abutment 272. As shown, the abutment 272 extends upwardly in the replica of the patient's mouth, beyond the adjacent tooth 274, and thus it requires reduction. As shown in FIG. 37B, the lab technician places a modification cap 278, in the form of an impression cap, over the abutment 272 in the stone model 270 and seats the modification cap 278 such that it fully engages the abutment 272 and is securely retained by the friction fit, as discussed above. Next, as shown in FIG. 37C, the lab technician removes the top of the modification cap 278 and then reduces the size of both the modification cap 278 and the abutment 272, until the abutment 272 reaches the desired size and shape. This results in the creation of a modified modification cap 282 surrounding a modified abutment 284. Next, the technician removes the modified modification cap 282 (shown in FIG. 37D) and fabricates a replacement tooth or crown to fit over the modified abutment 284.

Figure 37E:
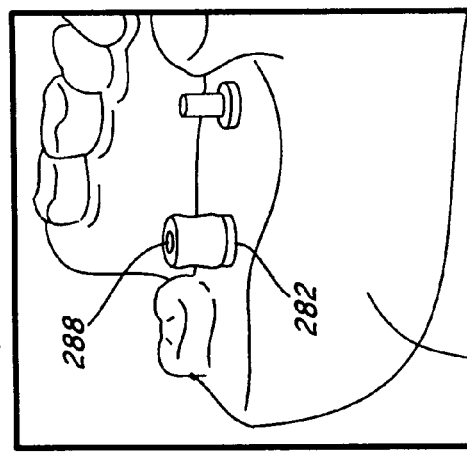
Figure 37F:
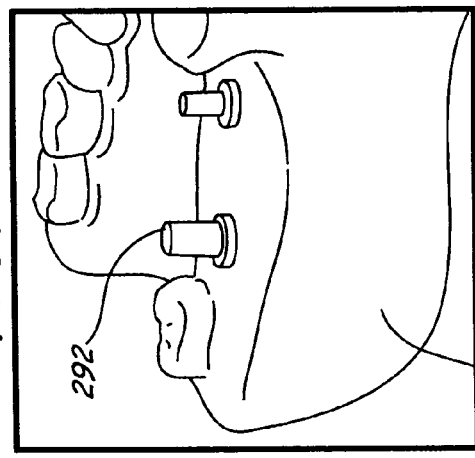

Once fabrication of the crown is completed, the lab technician sends both the crown and the modified modification cap 282 to the dentist. As shown in FIG. 37E, the dentist then places the modified modification cap 282 over the abutment 288 located in the patient's mouth 290, such that is fully engages the abutment 288. Full engagement with the abutment 288 is important to insure that an appropriate modification can be made to the abutment 288. The dentist then reduces the size of the abutment 288, using any known technique, to create a modified abutment 292 matching the modified modification cap 282 and thus the modified abutment 284 in the stone model. The dentist then removes the modified modification cap 282, as shown in FIG. 37F. The replacement tooth or crown is then connected to the modified abutment 292.

The impression cap, in accordance with the present invention, may also be used as a temporary cap for attaching a temporary crown. In this embodiment, the temporary crown is attached to or built up around the impression cap, which in turn is fit onto the dental implant 10 or the extension abutment 222. Preferably the impression cap has a white, opaque color to promote the natural look of the temporary crown. In this embodiment, the impression cap has a height such that it terminates short of the height of the surrounding teeth. This allows the temporary crown to be attached or built up around the impression cap, without negatively affecting the patient's bite. After the crown has been formed, the impression cap, with the formed temporary crown, is attached to the implant 10 or extension abutment 222 using a temporary adhesive or the like.

It should be understood that individual features of the above embodiments may stand alone as improvement or may be combined with each other in multiple configurations where physically possible. The proportional representation illustrated by the figures also represents structural disclosure of various embodiments.

The invention also contemplates sterilizing the impression cap via gamma sterilization. For this, a material must be chosen which is gamma sterilizable. Suitably a gamma sterilizable plastic, or more suitably a gamma sterilizable polypropylene, may be used.

The above described impression caps may be made by conventional means such as injection molding. Through injection molding, the caps may be a one piece structure. The invention also contemplates color-coding the separate pieces to denote abutment length and table collar diameter. The impression cap color corresponds to the appropriate color coded abutment and abutment analog. This may be done to aid the physician in matching the appropriate pieces. This is helpful considering the small sized of the pieces. The colors may be imparted into the material being molded into the cap.

If not described in detail above, the proportions and relative construction of the embodiments may be interpreted from the figures. Any inconsistencies between the figures and the description should be seen as alternative embodiments. Variations in the relative construction which do not change the inventive concepts presented herein are contemplated as possible embodiments of the invention.

Although the present invention has been described with reference to preferred embodiments, persons skilled in the art will recognize that changes may be made in form and detail without departing from the spirit and scope of the invention.

We claim:

1. A dental impression system comprising:
   one of a dental abutment or implant comprising:
   a proximal end,
   a distal end, and
   a collar positioned between said proximal and distal ends, said collar having an upper shoulder portion and a peripheral retention edge with an outer diameter, and
   an impression cap for coupling to said one dental abutment or implant comprising:
   a body having first and second ends and an inner cavity between said first and second ends, at least one of said first and second ends being an open end,
   a retention flange at said open end extending downwardly from the body in a direction generally parallel to a longitudinal centerline of the body, said flange having an inner retention surface engageable with said retention edge, said inner retention surface having a generally cylindrical configuration with a diameter slightly less than the outer diameter of said retention edge, such that, when the impression cap is fully coupled to said one dental abutment or implant, said inner retention surface forms a friction fit with said retention edge and a cylindrically shaped portion of said inner surface extends from said retention edge toward said distal end, and
   an inner angled surface located at the first end of the body, the inner angled surface having a size and an angle complementary to the upper shoulder portion and including an indentation, which defines a gap between the inner angled surface and the upper shoulder portion when the impression cap is coupled to the dental abutment or implant.

2. The impression system of claim 1 including a vent channel formed in the inner angled surface.

3. A dental impression system comprising:
   one of a dental abutment or implant comprising:
   a proximal end,
   a distal end, and
   a collar positioned between said proximal and distal ends, said collar having a peripheral retention edge with an outer diameter, and
   an impression cap for coupling to said one dental abutment or implant comprising:
   a body having first and second ends and an inner cavity between said first and second ends, wherein said first end is an open end and said second end is a substantially closed end and wherein the impression system further comprises a one-way vent positioned at said second end of the body, and
   a retention flange at said open end, said flange having an inner retention surface engageable with said retention edge, said inner retention surface having a generally cylindrical configuration with a diameter slightly less than the outer diameter of said retention edge, such that, when the impression cap is fully coupled to said one dental abutment or implant, said inner retention surface forms a friction fit with said retention edge and a cylindrically shaped portion of said inner surface extends from said retention edge toward said distal end.

4. The impression system of claim 3 wherein the one-way vent is adapted to allow air to exit said inner cavity of the body and to prevent external material from entering said inner cavity when the impression cap is encased in impression material.

5. A dental impression system comprising:
   one of a dental abutment or implant comprising:
   a proximal end,
   a distal end, and a collar positioned between said proximal and distal ends, said collar having a peripheral retention edge with an outer diameter, and an impression cap selectively connectable to and disconnectable from said one dental abutment or implant for taking an impression, said impression cap comprising:

a body having first and second ends and an inner cavity between said first and second ends, at least one of said first and second ends being an open end, a retention flange at said open end, said flange having an inner retention surface engageable with said retention edge to selectively connect said impression cap to said one dental abutment or implant, said inner retention surface having a generally cylindrical configuration with a diameter slightly less than the outer diameter of said retention edge, such that, when the impression cap is connected to said one dental abutment or implant, said inner retention surface forms a friction fit connection with said retention edge to connect said impression cap to said one dental abutment or implant solely by said friction fit connection, said inner retention surface further including a cylindrically shaped portion extending from said retention edge toward said distal end when the impression cap is connected with said one dental abutment or implant.

6. The impression system of claim 5 wherein the retention flange extends downwardly from the body in a direction generally parallel to a longitudinal centerline of the body.

7. The impression system of claim 6 wherein said collar includes an upper shoulder portion and said impression cap further comprises an inner angled surface located at the first end of the body, the inner angled surface having a size and an angle complementary to the upper shoulder portion.

8. The impression system of claim 7 wherein the inner angled surface extends circumferentially around the first end of the body.

9. The impression system of claim 5 wherein a leading edge of the retention flange includes a lead-in surface and an angled exterior surface.

10. The impression system of claim 9 wherein the lead-in surface has an angle complementary to the upper shoulder portion.

11. The impression system of claim 9 wherein the angled exterior surface extends at an angle of about 20 to about 25 degrees.

12. The impression system of claim 5 wherein the body is generally conical.

13. The impression system of claim 5 wherein said inner cavity of the body has an inner geometry that includes an internal abutment flat and has a size and shape complementary to said one dental abutment or implant.

14. The impression system of claim 5 wherein the impression cap is color coded to denote an abutment length and a collar diameter and to correspond to an appropriate color-coded abutment and abutment analog.

15. The impression system of claim 5 further comprising a temporary crown formed on an external surface of the body.

16. The impression system of claim 5 wherein said retention edge comprises the radially outermost portion of said one dental abutment or implant.

* * * * *